(12) United States Patent
Fujita et al.

(10) Patent No.: US 11,389,620 B2
(45) Date of Patent: Jul. 19, 2022

(54) CATHETER AND CATHETER KIT

(71) Applicant: SUMITOMO BAKELITE CO., LTD., Shinagawa-ku (JP)

(72) Inventors: Yasuhiro Fujita, Akita (JP); Yasushi Matsumoto, Sendai (JP); Taichi Shimizu, Osaka (JP); Yusaku Sugihara, Osaka (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 215 days.

(21) Appl. No.: 16/641,099

(22) PCT Filed: Aug. 24, 2018

(86) PCT No.: PCT/JP2018/031348
§ 371 (c)(1),
(2) Date: Feb. 21, 2020

(87) PCT Pub. No.: WO2019/039589
PCT Pub. Date: Feb. 28, 2019

(65) Prior Publication Data
US 2020/0188630 A1 Jun. 18, 2020

(30) Foreign Application Priority Data
Aug. 25, 2017 (JP) .............................. JP2017-162592

(51) Int. Cl.
*A61M 25/00* (2006.01)
*A61M 25/01* (2006.01)
(Continued)

(52) U.S. Cl.
CPC ........ *A61M 25/005* (2013.01); *A61M 25/002* (2013.01); *A61M 25/0067* (2013.01);
(Continued)

(58) Field of Classification Search
CPC .............. A61M 25/005; A61M 25/002; A61M 25/0067; A61M 25/0108; A61M 25/09
(Continued)

(56) References Cited

U.S. PATENT DOCUMENTS

2010/0094258 A1* 4/2010 Shimogami ......... A61M 25/005
606/191

FOREIGN PATENT DOCUMENTS

| CN | 102688550 A | 9/2012 |
| CN | 105879191 A | 8/2016 |

(Continued)

OTHER PUBLICATIONS

International Search Report dated Nov. 20, 2018 in PCT/JP2018/031348 filed Aug. 24, 2018, 1 page.

*Primary Examiner* — Phillip A Gray
(74) *Attorney, Agent, or Firm* — Oblon, McClelland, Maier & Neustadt, L.L.P.

(57) ABSTRACT

A catheter (100) includes a resin-made distal tip (80) linked to a distal end of a catheter body (10), and the distal tip (80) has a distal lumen (81) having an open distal end. The distal lumen (81) communicates with a lumen (31). The catheter (100) is an inactive type microcatheter in which an outer diameter of the distal end of the catheter body (10) is 0.6 mm or smaller and a maximum outer diameter of the distal tip (80) is 0.6 mm or smaller. A dimension of a marker (70) in an axial direction of the catheter body (10) is smaller than the maximum outer diameter of the distal tip (80), and the length of the distal tip (80) in the axial direction of the distal tip (80) is 3 times to 18 times the maximum outer diameter of the distal tip (80).

20 Claims, 17 Drawing Sheets

(51) Int. Cl.
*A61M 25/09* (2006.01)
*A61L 29/08* (2006.01)

(52) U.S. Cl.
CPC ........ *A61M 25/0108* (2013.01); *A61M 25/09* (2013.01); *A61L 29/085* (2013.01); *A61M 2025/0042* (2013.01); *A61M 2025/09191* (2013.01); *A61M 2205/02* (2013.01)

(58) Field of Classification Search
USPC ........................................................ 604/524
See application file for complete search history.

(56) References Cited

FOREIGN PATENT DOCUMENTS

| | | |
|---|---|---|
| JP | 2007-82802 A | 4/2007 |
| JP | 2007-236472 A | 9/2007 |
| JP | 2010-88833 A | 4/2010 |

* cited by examiner

CATHETER AND CATHETER KIT

TECHNICAL FIELD

The present invention relates to a catheter and a catheter kit.

Priority is claimed on Japanese Patent Application No. 2017-162592, filed on Aug. 25, 2017, the content of which is incorporated herein by reference.

BACKGROUND ART

In recent years, a catheter that can be inserted into a body cavity such as a blood vessel has been developed (for example, Patent Document 1).

In general, the catheter is inserted into the body cavity by an over-the-wire method using a guide wire. According to this method, a distal portion of the guide wire inserted into the catheter is projected from a distal end of the catheter. After a distal end of the guide wire reaches a desired bifurcated path, the catheter is pushed along the guide wire so that the catheter is inserted into the desired bifurcated path.

CITATION LIST

Patent Literature

[Patent Document 1] Japanese Unexamined Patent Application, First Publication No. 2007-82802 A

SUMMARY OF INVENTION

Technical Problem

Human blood vessels include a blood vessel called a relatively narrow perforator bifurcated from a relatively wide blood vessel. In a case where a desired bifurcated path is a narrow blood vessel such as the perforator, an AVM, a vertebral artery, or a vasa vasorum connected to a tumor, even a skilled operator cannot always easily insert a commercially available catheter into the blood vessel to reach a sufficient depth position of the bifurcated path.

The present invention is made in view of the above-described problem, and aims to provide a catheter and a catheter kit which have a structure enabling a medical procedure to be preferably performed so that the catheter is guided by a guide wire to enter the narrow blood vessel such as the perforator, the AVM, the vertebral artery, or the vasa vasorum connected to the tumor.

Solution to Problem

The present application includes the following aspects.

(1) There is a catheter including a catheter body having a resin layer including an inner layer having a lumen and an outer layer formed in an outer periphery of the inner layer, and a reinforcement layer incorporated in the resin layer and disposed around the lumen, a ring-shaped marker made of a radiopaque metal material, the marker being incorporated in the resin layer in a distal end of the catheter body, fixed to a distal end of the reinforcement layer, and disposed around the lumen, and a distal tip made of a resin linked to the distal end of the catheter body, the distal tip having a distal lumen which communicates with the lumen and has an open distal end. An outer diameter of the distal end of the catheter body is 0.6 mm or smaller, a maximum outer diameter of the distal tip is 0.6 mm or smaller. A dimension of the marker in an axial direction of the catheter body is smaller than the maximum outer diameter of the distal tip. The length of the distal tip in the axial direction of the distal tip is 3 times to 18 times the maximum outer diameter of the distal tip.

(2) In the catheter according to (1), a portion of the reinforcement layer disposed in a distal portion of the catheter body is configured to include a braid in which wires are braided. A pitch of the wires is larger than an outer diameter of the distal portion of the catheter body.

(3) In the catheter according to (1) or (2), an outer diameter of the distal tip is constant regardless of a position of the distal tip in the axial direction.

(4) In the catheter according to (1) or (2), the distal tip has a first constant diameter region whose outer diameter and inner diameter are constant regardless of a position of the distal tip in the axial direction, a reduced diameter region connected to a distal side of the first constant diameter region and whose outer diameter and inner diameter are reduced toward the distal side, and a second constant diameter region connected to a distal side of the reduced diameter region and whose outer diameter and inner diameter are constant regardless of a position of the distal tip in the axial direction.

(5) In the catheter according to any one of (1) to (4), the catheter body has a first distal region connected to a proximal side of the distal tip, and a second distal region connected to a proximal side of the first distal region. The first distal region is made of a resin material which is the same as that of the distal tip. The second distal region is made of a resin material which is harder than the resin material forming the first distal region. The reinforcement layer is continuously disposed throughout the first distal region and the second distal region.

(6) In the catheter according to (5), the catheter body has an enlarged diameter region in which the inner diameter of the lumen and the outer diameter of the catheter body are gradually enlarged toward the proximal side, and the enlarged diameter region is closer to the proximal side than the second distal region.

(7) In the catheter according to (6), in a region from the distal side of the enlarged diameter region to the proximal side of the enlarged diameter region in the catheter body, the resin layer is made of the same resin material.

(8) In the catheter according to (6) or (7), a region adjacent to the proximal side of the enlarged diameter region in the catheter body is a small diameter region having the same outer diameter as a proximal end of the enlarged diameter region. A region adjacent to the proximal side of the small diameter region in the catheter body is a large diameter region having a larger diameter than the small diameter region.

(9) In the catheter according to any one of (1) to (8), the distal tip has Shore D hardness of 40 or lower.

(10) In the catheter according to any one of (1) to (9), a proximal side portion in the reinforcement layer from an intermediate portion in a longitudinal direction of the catheter body is configured to include a first braid, and a second braid braided in an outer periphery of the first braid. A cross-sectional area of each wire forming the second braid is larger than a cross-sectional area of each wire forming the first braid.

(11) There is a catheter kit including the catheter according to (4), and a guide wire used by being inserted into the lumen. The inner diameter of the second constant diameter region is the same as the outer diameter of the distal portion of the guide wire.

Advantageous Effects of Invention

According to the present invention, a medical procedure can be preferably performed so that the catheter is guided by the guide wire to enter the narrow blood vessel such as the perforator, the AVM, the vertebral artery, or the vasa vasorum connected to the tumor.

DESCRIPTION OF EMBODIMENTS

Figure 1:
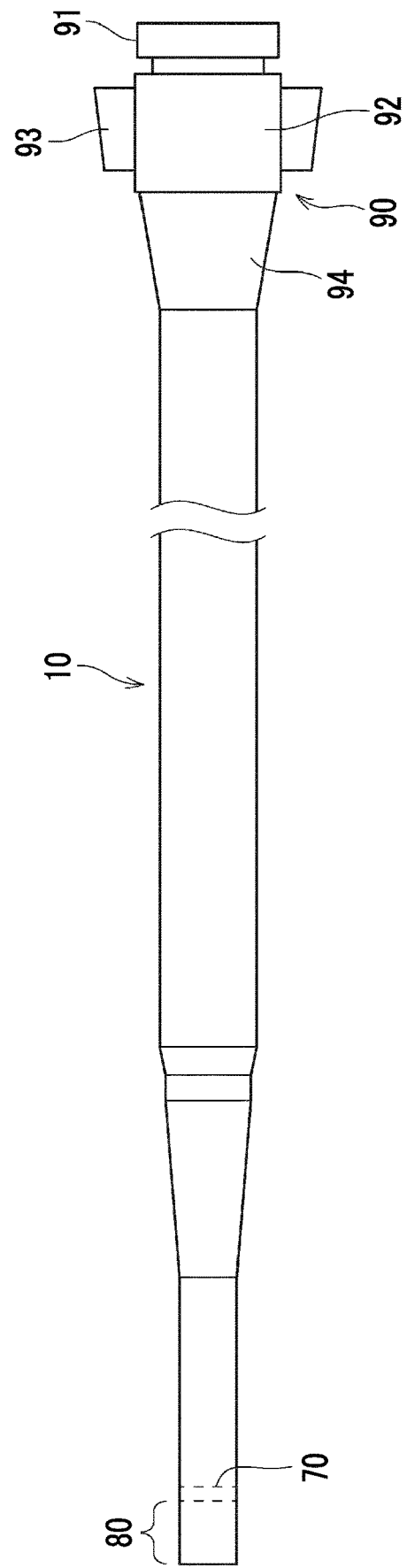
FIG. 1 is an overall view of a catheter according to a first embodiment.

Hereinafter, embodiments of the present invention will be described with reference to the drawings. In all of the drawings, the same reference numerals will be given to the same configuration elements, and description thereof will be omitted as appropriate.

Various configuration elements of a catheter according to the present embodiment do not need to be individually independent. The followings are permitted. A plurality of configuration elements are formed as one member. One configuration element is formed of a plurality of members. A certain configuration element is a part of another configuration element. A part of a certain configuration element overlaps a part of another configuration element.

Terms used in describing the embodiments of the present invention are defined as follows, unless otherwise specified.

In describing the embodiments, the terms of a distal portion and a proximal portion may be used as appropriate, in some cases. The distal portion refers to a predetermined length region including an end (distal end) on an insertion distal side of a catheter in each portion of the catheter. In addition, the proximal portion refers to a predetermined length region including an end (proximal end) on a proximal side of the catheter in each portion of the catheter.

In addition, an axis means a central axis extending along a longitudinal direction of a catheter body.

A longitudinal cross section of the catheter refers to a cross section obtained by cutting the catheter along the axis.

First Embodiment

First, a first embodiment will be described with reference to FIGS. 1 to 9.

Figure 2:
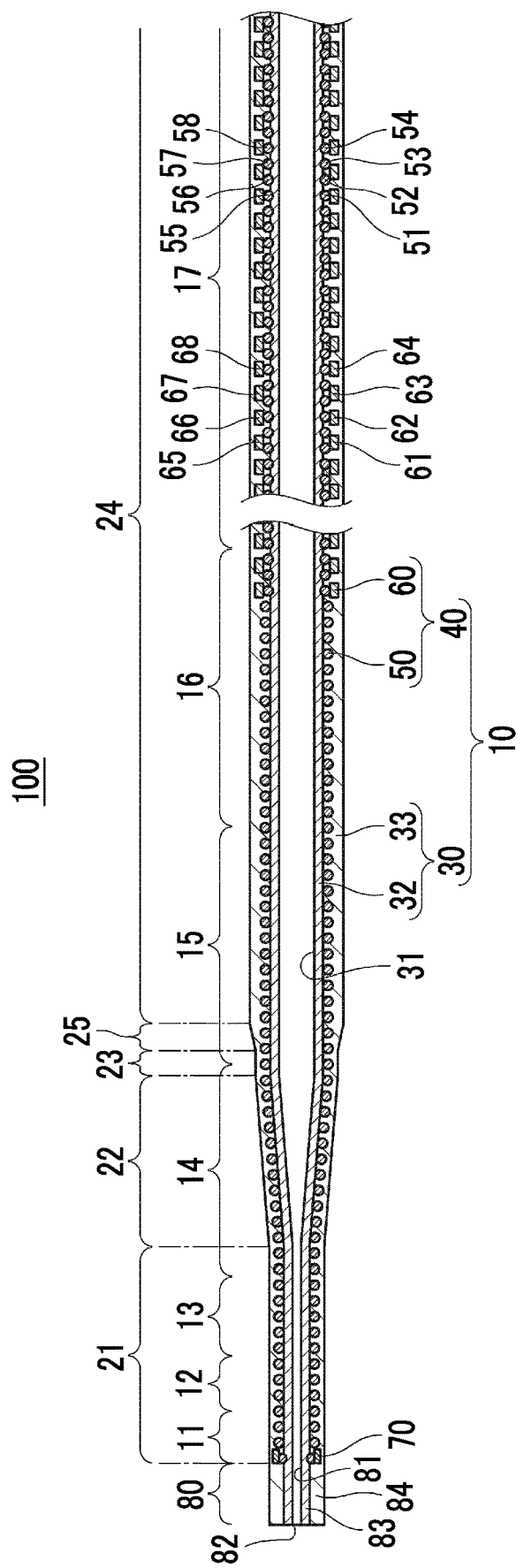
FIG. 2 is a longitudinal sectional view of the catheter according to the first embodiment.
Figure 3:
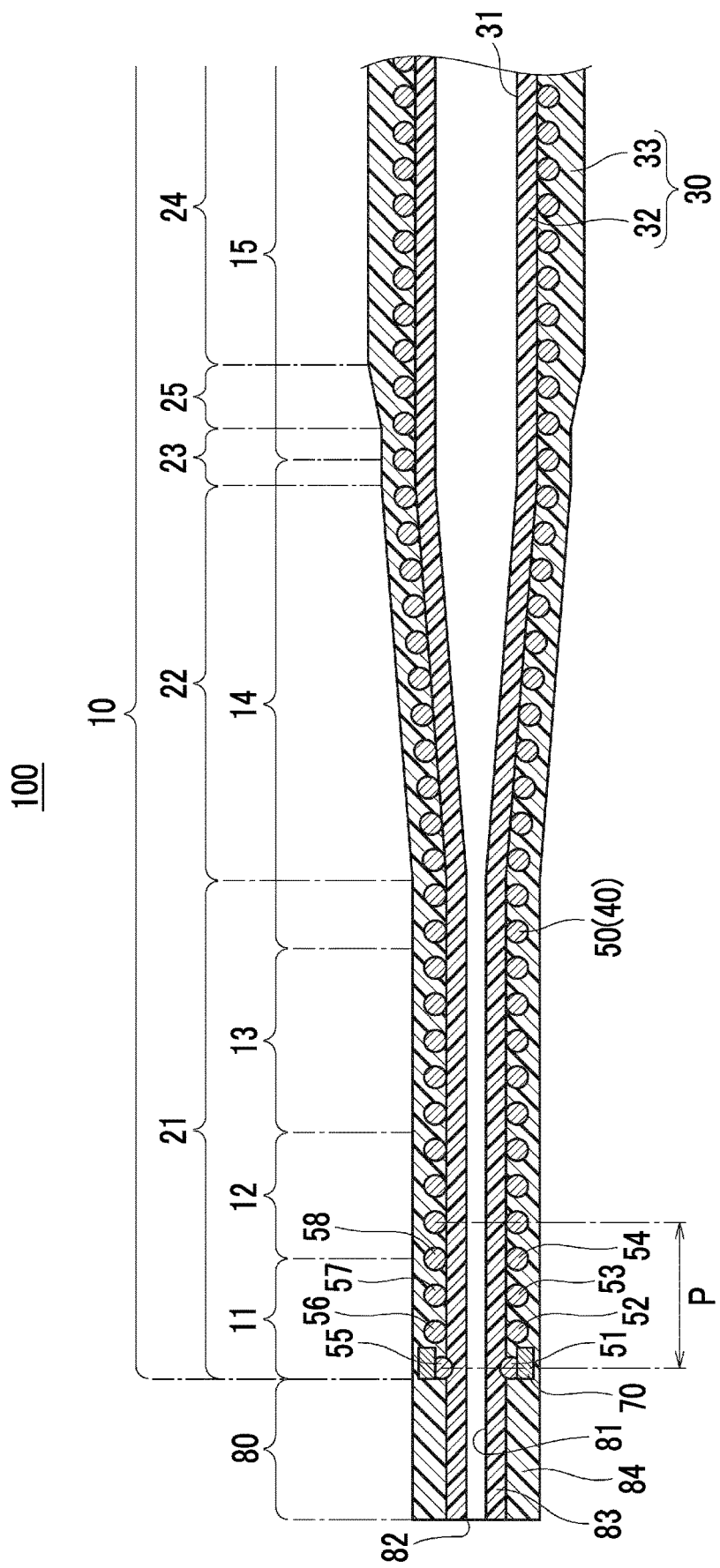
FIG. 3 is a partially enlarged view of FIG. 2, which shows a distal portion of the catheter.

As shown in any of FIGS. 1 to 3, a catheter 100 according to the present embodiment includes an elongated catheter body 10 having a resin layer 30 including an inner layer 32 having a lumen 31 and an outer layer 33 formed in an outer periphery of the inner layer 32, and a reinforcement layer 40 incorporated in the resin layer 30 and disposed around the lumen 31.

Furthermore, the catheter 100 includes a ring-shaped marker 70 made of a radiopaque metal material (for example, a platinum alloy). The marker 70 is incorporated in the resin layer 30 in a distal end of the catheter body 10, is fixed to a distal end of the reinforcement layer 40, and is disposed around the lumen 31.

Furthermore, the catheter 100 includes a resin-made distal tip 80 linked to the distal end of the catheter body 10. The distal tip 80 has a distal lumen 81 having an open distal end, and the distal lumen 81 communicates with the lumen 31. Hereinafter, an opening in the distal end of the distal lumen 81 will be referred to as a distal opening 82.

The catheter 100 is an inactive type microcatheter in which an outer diameter of the distal end of the catheter body 10 is 0.6 mm or smaller and a maximum outer diameter of the distal tip 80 is 0.6 mm or smaller. Here, the inactive type means a device that changes a curvature of at least a portion of the catheter in a blood vessel and does not depend on electric energy or other power sources (power sources other than power generated by a human body or gravity).

A dimension (length) of the marker 70 in the axial direction of the catheter body 10 is smaller than a maximum outer diameter of the distal tip 80.

Then, a length of the distal tip 80 in the axial direction of the distal tip 80 is 3 times to 18 times the maximum outer diameter of the distal tip 80.

In a case of the present embodiment, as will be described later, the reinforcement layer disposed on a distal side of the catheter body 10 is a braid (first braid 50).

In this case, the length of the distal tip 80 in the axial direction of the distal tip 80 is preferably 4 times to 18 times the maximum outer diameter of the distal tip 80, more preferably 7 times to 15 times, and much more preferably 8 times to 12 times.

In each of FIGS. 1 to 3, dimensions of the catheter body 10 and the distal tip 80 in a radial direction are significantly enlarged in the illustration.

According to the catheter 100 having this configuration, a medical procedure can be preferably performed so that the catheter 100 enters a narrow blood vessel such as a perforator, an AVM, a vertebral artery, or a vasa vasorum connected to a tumor. For example, as shown in time-series operation examples in FIGS. 4A, 4B, 5A, 5B, and 6 or FIGS. 7A, 7B, and 8, a medical procedure can be preferably performed so that the catheter 100 enters a small diameter blood vessel (for example, a perforator 302) bifurcated from a relatively large diameter artery (internal carotid artery 301) through the artery.

That is, the distal tip 80 is configured to be sufficiently soft (as will be described later, Shore D hardness of the distal tip 80 is 40 or lower, for example). In this manner, while the distal tip 80 can satisfactorily follow a bent shape of a guide wire 200, the distal tip 80 can enter the perforator 302 along the guide wire 200.

In particular, a medical procedure can be preferably performed so that the catheter 100 enters the perforator 302 through the internal carotid artery 301 having an inner diameter of approximately 5 mm.

Hereinafter, the present embodiment will be described in more detail.

In a case of the present embodiment, the resin layer 30 forming the catheter body 10 has a layer structure including an inner layer 32 and an outer layer 33 which are respectively made of a resin material. The resin layer 30 may be configured to include a hydrophilic coat (to be described below).

The inner layer 32 has a hollow tube structure. The lumen 31 is an internal space of the inner layer 32. The lumen 31 is continuously formed from the distal end to the proximal end of the catheter body 10, and the distal end and the proximal end of the catheter body 10 are respectively open.

The outer layer 33 has a hollow tube structure coaxial with the inner layer 32, and an inner peripheral surface of the outer layer 33 is joined to an outer peripheral surface of the inner layer 32.

A resin material forming the inner layer 32 and a resin material forming the outer layer 33 may be different from each other, or may be equal to each other.

The distal tip 80 has the same layer structure as the resin layer 30 of the catheter body 10. That is, the distal tip 80 has a two layer structure having the inner layer 83 and the outer layer 84.

The inner layer 83 has a hollow tube structure. The distal lumen 81 is an internal space of the inner layer 83. The distal lumen 81 is continuously formed from the distal end to the proximal end of the distal tip 80. The proximal end of the distal lumen 81 communicates with the distal end of the lumen 31. The distal lumen 81 is open in the distal end (distal opening 82).

The inner layer 83 is linked to the distal side of the inner layer 32.

The outer layer 84 is linked to the distal side of the outer layer 33.

The inner diameter and the outer diameter of the inner layer 32 in the distal end of the catheter body 10 are equal to the inner diameter and the outer diameter of the inner layer 83 in the proximal end of the distal tip 80.

The inner diameter and the outer diameter of the outer layer 33 in the distal end of the catheter body 10 are equal to the inner diameter and the outer diameter of the outer layer 84 in the proximal end of the distal tip 80.

In a case of the present embodiment, the outer diameter of the distal tip 80 is constant regardless of a position of the distal tip 80 in an axial direction.

Here, a fact that the inner diameter and the outer diameter of the distal tip 80 are constant regardless of the position of the distal tip 80 in the axial direction means that a change in the outer diameter and a change in the inner diameter of the distal tip 80 which correspond to the position of the distal tip 80 in the axial direction respectively fall within a range of ±10%, and each of the changes preferably falls within a range of ±5%.

A corner portion on an outer peripheral side of the distal end of the distal tip 80 may have an R-chamfered shape. In this case, except for a distal region where the corner portion has the R-chamfered shape in the axial direction of the distal tip 80, the outer diameter of the distal tip 80 is constant regardless of the position of the distal tip 80 in the axial direction.

The Shore D hardness of the distal tip 80 is 40 or lower. It is preferable that the Shore D hardness of the distal tip 80 is 20 or higher. The Shore D hardness is determined in accordance with ISO868.

Here, the Shore D hardness of the distal tip 80 is the Shore D hardness on an outer surface side of the distal tip 80. In a case of the present embodiment, the Shore D hardness is the Shore D hardness of the outer layer 84.

In the case of the present embodiment, the reinforcement layer 40 is disposed around the inner layer 32 so as to surround the inner layer 32.

The reinforcement layer 40 is configured to include a first braid 50 and a second braid 60 disposed in an outer periphery of the first braid 50.

More specifically, for example, the first braid 50 is continuously disposed from the distal end to the proximal end of the catheter body 10 (refer to FIGS. 2 and 3).

On the other hand, for example, the second braid 60 is continuously disposed from an intermediate portion to the proximal end of the catheter body 10, but is not disposed in the distal portion of the catheter body 10 (refer to FIG. 2).

The first braid 50 is configured so that a plurality of wires are braided. Preferably, the first braid 50 is configured so that the plurality of wires by the plurality of wires are wound in mutually opposite directions.

As an example, the first braid 50 is configured so that eight wires of a first wire 51 to an eighth wire 58 are braided. However, the number of wires forming the first braid 50 is not limited to this example.

Each of these wires is a single wire (not a stranded wire), for example. A cross-sectional shape of these wires is not particularly limited. However, for example, a circular shape may be adopted. That is, the wire forming the first braid 50 is a round wire, for example. The outer diameters of the first wire 51 to the eighth wire 58 are equal to each other, for example.

Out of the wires forming the first braid 50, four wires of the first wire 51, the second wire 52, the third wire 53, and the fourth wire 54 spirally extend parallel to each other. That is, the first wire 51 to the fourth wires 54 are spirally wound around the inner layer 32 at a substantially equal interval in the axial direction of the catheter body 10.

The remaining fifth wire 55, sixth wire 56, seventh wire 57, and eighth wire 58 spirally extend parallel to each other. That is, the fifth wire 55 to the eighth wire 58 are spirally wound around the inner layer 32 at a substantially equal interval in the axial direction of the catheter body 10.

However, a turning direction of a spiral formed by the first wire 51 to the fourth wire 54 and a turning direction of a spiral formed by the fifth wire 55 to the eighth wire 58 are mutually opposite directions (opposite to each other). Therefore, the first wire 51 to the fourth wire 54 and the fifth wire 55 to the eighth wire 58 periodically intersect each other in the axial direction of the catheter body 10.

In a case of the present embodiment, each pitch P (FIG. 3) of the wires forming the first braid 50 is larger than the outer diameter of the distal portion (for example, a distal side small diameter region 21 to be described later) of the catheter body 10. Here, as shown in FIG. 3, with regard to the pitch P of the first wire 51, the pitch P is an inter-axis distance of a pair of adjacent winding portions in each wire.

In this way, a portion of the reinforcement layer 40 which is disposed in the distal portion (for example, the distal side small diameter region 21) of the catheter body 10 is configured to include the braid (first braid 50) in which the wires (for example, the first wire 51 to the eighth wire 58) are braided. The pitch of the wires is larger than the outer diameter of the distal portion of the catheter body 10.

According to this structure, wrinkle forming on the outer surface of the inner layer 32 can be suppressed. The outer surface of the inner layer 32 can be flattened, and the thickness of the inner layer 32 can be uniform in the axial direction of the catheter body 10. In addition, according to this structure, both stiffness and flexibility of the distal portion of the catheter body 10 can be properly and compatibly achieved.

For example, the first braid 50 is configured so that the wires are wound at a constant pitch from the distal end to the proximal end of the first braid 50.

The second braid 60 is configured by braiding a plurality of wires.

As an example, the second braid 60 is configured so that the eight wires of the first wire 61 to the eighth wire 68 are braided. However, the number of wires forming the second braid 60 is not limited to this example.

Each of these wires is a single wire (not a stranded wire), for example. The cross-sectional shape of these wires is not particularly limited. However, for example, a flat rectangular shape is adopted. That is, the wire forming the second braid 60 is a rectangular wire, for example. The cross-sectional shapes and cross-sectional areas of the first wire 61 to the eighth wire 68 are equal to each other, for example.

Out of the wires forming the second braid 60, the four wires of the first wire 61, the second wire 62, the third wire 63, and the fourth wire 64 spirally extend parallel to each other. That is, the first wire 61 to the fourth wires 64 are spirally wound around the first braid 50 at a substantially equal interval in the axial direction of the catheter body 10.

The remaining fifth wire 65, sixth wire 66, seventh wire 67, and eighth wire 68 spirally extend parallel to each other. That is, the fifth wire 65 to the eighth wire 68 are spirally wound around the first braid 50 at a substantially equal interval in the axial direction of the catheter body 10.

However, a turning direction of a spiral formed by the first wire 61 to the fourth wire 64 and a turning direction of a spiral formed by the fifth wire 65 to the eighth wire 68 are mutually opposite directions (opposite to each other). Therefore, the first wire 61 to the fourth wire 64 and the fifth wire 65 to the eighth wire 68 periodically intersect each other in the axial direction of the catheter body 10.

Here, the cross-sectional area of the first wire 61 to the eighth wire 68 forming the second braid 60 is larger than the cross-sectional area of the first wire 51 to the eighth wire 58 forming the first braid 50.

That is, a proximal side portion of the reinforcement layer 40 from the intermediate portion in the longitudinal direction of the catheter body 10 is configured to include the first braid 50 and the second braid 60 braided in the outer periphery of the first braid 50. The cross-sectional area of each wire forming the second braid 60 is larger than the cross-sectional area of each wire forming the first braid 50.

In this manner, the portion from the intermediate portion to the proximal side portion of the catheter body 10 can have sufficiently ensured rigidity. Accordingly, pushing ability of the catheter 100 can be satisfactorily realized.

The ring-shaped marker 70 is disposed around the inner layer 32 coaxially with the inner layer 32 and the outer layer 33.

As described above, the marker 70 is fixed to the distal end of the reinforcement layer 40. More specifically, for example, the marker 70 is disposed around the distal end of the first braid 50, and is fixed to the distal end of the first braid 50 by means of caulking. However, the marker 70 may be linked to the distal side of the first braid 50 by being joined to the distal side of the distal end of the first braid 50.

As described above, a dimension of the marker 70 in the axial direction of the catheter body 10, that is, an axial length of the marker 70 is smaller than the maximum outer diameter of the distal tip 80.

The axial length of the marker 70 is preferably 0.2 mm to 0.4 mm, and can be typically set to approximately 0.3 mm.

In addition, the axial length of the marker 70 is preferably shorter than the outer diameter of the marker 70, and more preferably shorter than the inner diameter of the marker 70.

As shown in FIG. 3, the catheter body 10 has a first distal region 11 connected to the proximal side of the distal tip 80, and a second distal region 12 connected to the proximal side of the first distal region 11.

The first distal region 11 is made of the same resin material as the distal tip 80. More specifically, a resin material forming the inner layer 32 in the first distal region 11 and a resin material forming the inner layer 83 of the distal tip 80 are the same material. A resin material forming the outer layer 33 in the first distal region 11 and a resin material forming the outer layer 84 of the distal tip 80 are the same material.

The second distal region 12 is made of the resin material harder than the resin material forming the first distal region 11. More specifically, for example, the inner layer 32 is made of the same resin material from the distal end to the proximal end of the catheter body 10. Therefore, the resin material forming the inner layer 32 in the second distal region 12 and the resin material forming the inner layer 32 in the first distal region 11 are the same material. However, the resin material forming the outer layer 33 in the second distal region 12 is harder than the resin material forming the outer layer 33 in the first distal region 11. For example, in a case where both the outer layer 33 in the second distal region 12 and the outer layer 33 in the first distal region 11 are made of a polyether block amide copolymer, as the polyether block amide copolymer forming the outer layer 33 in the second distal region 12, the copolymer having the Shore D hardness higher than the Shore D hardness of the polyether block amide copolymer forming the outer layer 33 in the first distal region 11 is selected.

Then, the reinforcement layer 40 is continuously disposed throughout the first distal region 11 and the second distal region 12. More specifically, as shown in FIG. 3, the first braid 50 is continuously disposed throughout the first distal region 11 and the second distal region 12.

According to this configuration, the rigidity of the distal portion of the catheter body 10 can be gradually improved toward the proximal side. Accordingly, the pushing ability in the distal portion of the catheter body 10 can be properly realized. An excessive and discontinuous change in the rigidity can be suppressed in a boundary between the first distal region 11 and the second distal region 12.

For example, the Shore D hardness of the second distal region 12 can be 1.1 times to 1.2 times the Shore D hardness of the distal tip 80 and the first distal region 11.

The Shore D hardness of the first distal region 11 and the second distal region 12 is the Shore D hardness of each outer surface side.

The catheter body 10 has an enlarged diameter region 22 in which the inner diameter of the lumen 31 and the outer diameter of the catheter body 10 are gradually enlarged toward the proximal side. The enlarged diameter region 22 is closer to the proximal side than the second distal region 12.

For example, in the enlarged diameter region 22, the inner diameter of the lumen 31 and the outer diameter of the catheter body 10 are gradually enlarged in a linearly tapered shape toward the proximal side.

According to this configuration, the rigidity of the catheter body 10 can be gradually improved toward the proximal side in the enlarged diameter region 22, and the pushing ability of the catheter body 10 can be satisfactorily realized.

In addition, a liquid such as a drug solution can be smoothly supplied to the distal portion of the catheter body 10 via the lumen 31.

In a region (fourth distal region 14 shown in FIG. 3) of the catheter body 10 from the distal side of the enlarged diameter region 22 to the proximal side of the enlarged diameter region 22, the resin layer 30 is made of the same resin material. More specifically, the material of the inner layer 32 is the same resin material (for example, PTFE) from the distal end to the proximal end of the fourth distal region 14, and the material of the outer layer 33 is the same resin material (for example, a polyether block amide copolymer) from the distal end to the proximal end of the fourth distal region 14.

According to this configuration, a discontinuous change in the rigidity can be suppressed in a boundary between the enlarged diameter region 22 and a region (distal side small diameter region 21 shown in FIG. 3) adjacent to the distal side of the enlarged diameter region 22 in the catheter body 10. In addition, a discontinuous change in the rigidity can be suppressed in a boundary between the enlarged diameter region 22 and a region (small diameter region 23 shown in FIG. 3) adjacent to the proximal side of the enlarged diameter region 22 in the catheter body 10.

Therefore, each kink occurrence can be suppressed in the distal end and the proximal end of the enlarged diameter region 22.

As shown in FIG. 3, a region adjacent to the proximal side of the enlarged diameter region 22 in the catheter body 10 is a small diameter region 23 having the same outer diameter as the proximal end of the enlarged diameter region 22. A region adjacent to the proximal side of the small diameter region 23 in the catheter body 10 is a large diameter region 24 having the larger diameter than the small diameter region 23.

The proximal side of the catheter body 10 includes the large diameter region 24. Accordingly, the portion on the proximal side of the catheter body 10 can have sufficiently ensured rigidity, and the pushing ability of the catheter 100 can be satisfactorily realized.

For example, an outer diameter change region 25 whose outer diameter gradually increases toward the proximal side is disposed between the small diameter region 23 and the large diameter region 24.

In addition, for example, in the portions (small diameter region 23, outer diameter change region 25, and large diameter region 24) on the proximal side of the enlarged diameter region 22 in the catheter body 10, the inner diameter of the lumen 31 is constant.

In addition, for example, a region on the distal side of the enlarged diameter region 22 in the catheter body 10 is a distal side small diameter region 21 whose inner diameter and outer diameter are constant regardless of the position of the catheter body 10 in the axial direction.

The inner diameter (inner diameter of the lumen 31) and the outer diameter of the distal side small diameter region 21 are equal to the inner diameter and the outer diameter of the distal end of the enlarged diameter region 22.

Here, a fact that the inner diameter and the outer diameter of the distal side small diameter region 21 are constant regardless of the position of the catheter body 10 in the axial direction means that a change in the outer diameter and a change in the inner diameter of the distal side small diameter region 21 which correspond to the position of the catheter body 10 in the axial direction respectively fall within a range of ±10%, and each of the changes preferably falls within a range of ±5%.

For example, the distal side small diameter region 21 includes the first distal region 11 and the second distal region 12 as described above, and additionally includes a third distal region 13.

The third distal region 13 is connected to the proximal side of the second distal region 12. The third distal region 13 is made of a resin material which is harder than the resin material forming the second distal region 12. More specifically, the resin material forming the inner layer 32 in the second distal region 12 and the resin material forming the inner layer 32 in the third distal region 13 are the same material. However, the resin material forming the outer layer 33 in the third distal region 13 is harder than the resin material forming the outer layer 33 in the second distal region 12. For example, in a case where the resin material forming the outer layer 33 in the second distal region 12 and the outer layer 33 in the third distal region 13 is a polyether block amide copolymer, as the polyether block amide copolymer forming the outer layer 33 in the third distal region 13, the copolymer having the Shore D hardness higher than the Shore D hardness of the polyether block amide copolymer forming the outer layer 33 in the second distal region 12 is selected.

Then, the first braid 50 is continuously disposed throughout the second distal region 12 and the third distal region 13.

Furthermore, the distal side small diameter region 21 includes the distal portion of the fourth distal region 14.

The proximal end of the fourth distal region 14 is located in an intermediate portion between the distal end and the proximal end of the small diameter region 23 described above.

The fourth distal region 14 is made of a resin material which is harder than the resin material forming the third distal region 13. More specifically, the resin material forming the inner layer 32 in the third distal region 13 and the resin material forming the inner layer 32 in the fourth distal region 14 are the same material. However, the resin material forming the outer layer 33 in the fourth distal region 14 is harder than the resin material forming the outer layer 33 in the third distal region 13. For example, in a case where the resin material forming the outer layer 33 in the third distal region 13 and the outer layer 33 in the fourth distal region 14 is a polyether block amide copolymer, as the polyether block amide copolymer forming the outer layer 33 in the fourth distal region 14, the copolymer having the Shore D hardness higher than the Shore D hardness of the polyether block amide copolymer forming the outer layer 33 in the third distal region 13 is selected.

The catheter body 10 further includes a fifth distal region 15 connected to the proximal side of the fourth distal region 14, a sixth distal region 16 connected to the proximal side of the fifth distal region 15, and an intermediate/proximal region 17 connected to the proximal side of the sixth distal region 16.

The fifth distal region 15 is made of a resin material which is harder than the resin material forming the fourth distal region 14. More specifically, the resin material forming the inner layer 32 in the fourth distal region 14 and the resin material forming the inner layer 32 in the fifth distal region 15 are the same material. However, the resin material forming the outer layer 33 in the fifth distal region 15 is harder than the resin material forming the outer layer 33 in the fourth distal region 14. For example, in a case where the resin material forming the outer layer 33 in the fourth distal region 14 and the outer layer 33 in the fifth distal region 15 is a polyether block amide copolymer, as the polyether block amide copolymer forming the outer layer 33 in the fifth distal region 15, the copolymer having the Shore D hardness higher than the Shore D hardness of the polyether block amide copolymer forming the outer layer 33 in the fourth distal region 14 is selected.

The sixth distal region 16 is made of a resin material which is harder than the resin material forming the fifth distal region 15. More specifically, the resin material forming the inner layer 32 in the fifth distal region 15 and the resin material forming the inner layer 32 in the sixth distal region 16 are the same material. However, the resin material forming the outer layer 33 in the sixth distal region 16 is harder than the resin material forming the outer layer 33 in the fifth distal region 15. For example, in a case where the resin material forming the outer layer 33 in the fifth distal region 15 and the outer layer 33 in the sixth distal region 16 is a polyether block amide copolymer, as the polyether block amide copolymer forming the outer layer 33 in the sixth distal region 16, the copolymer having the Shore D hardness higher than the Shore D hardness of the polyether block amide copolymer forming the outer layer 33 in the fifth distal region 15 is selected.

The intermediate/proximal region 17 is made of a resin material which is harder than the resin material forming the sixth distal region 16. More specifically, the resin material forming the inner layer 32 in the sixth distal region 16 and the resin material forming the inner layer 32 in the intermediate/proximal region 17 are the same material. However, the resin material forming the outer layer 33 in the intermediate/proximal region 17 is harder than the resin material forming the outer layer 33 in the sixth distal region 16. For example, in a case where the resin material forming the outer layer 33 in the sixth distal region 16 and the outer layer 33 in the intermediate/proximal region 17 is a polyether block amide copolymer, as the polyether block amide copolymer forming the outer layer 33 in the intermediate/proximal region 17, the copolymer having the Shore D hardness higher than the Shore D hardness of the polyether block amide copolymer forming the outer layer 33 in the sixth distal region 16 is selected.

The small diameter region 23 includes the distal portion of the fifth distal region 15.

The outer diameter change region 25 is configured to include another portion of the fifth distal region 15.

The distal portion of the large diameter region 24 is configured to include still another portion of the fifth distal region 15, the sixth distal region 16, and the intermediate/proximal region 17.

For example, the distal end of the second braid 60 is located in the proximal portion of the sixth distal region 16.

In addition, if necessary, a hydrophilic coat may be formed on the outer surface layer of the distal side portion of the catheter body 10 and the outer surface layer of the distal tip 80. For example, the hydrophilic coat is formed on the outer surface layer from the distal portion of the intermediate/proximal region 17 to the distal end of the catheter body 10, and on the outer surface layer of the distal tip 80.

Here, a dimension example of each portion of the catheter 100 will be described.

The length of the distal tip 80 in the axial direction of the distal tip 80 is preferably from 2.5 mm to 7 mm, more preferably from 3 mm to 7 mm, and much more preferably from 4 mm to 6 mm. Typically, the length can be approximately 5 mm. The length of the distal tip 80 is preferably set to the length equal to the inner diameter of a relatively large diameter blood vessel (such as an internal carotid artery) before the blood vessel is bifurcated into a small diameter blood vessel such as a perforator.

The length of the first distal region 11 in the axial direction of the catheter body 10 is preferably 3 mm to 7 mm. Typically, the length can be approximately 5 mm.

The length of the second distal region 12 in the axial direction of the catheter body 10 is preferably 5 mm to 15 mm. Typically, the length can be approximately 10 mm.

An effective length of the catheter 100 including the distal tip 80 and a portion that can be inserted into a body cavity in the catheter body 10 is preferably 130 cm to 200 cm. Typically, the effective length can be approximately 165 cm.

The maximum outer diameter of the distal tip 80 is 0.6 mm or smaller as described above. The maximum outer diameter of the distal tip 80 is more preferably 0.5 mm or smaller. The maximum outer diameter of the distal tip 80 is preferably 0.35 mm or larger. Typically, the maximum outer diameter can be 0.4 min to 0.45 mm.

The outer diameter of the distal side small diameter region 21 is 0.6 mm or smaller as described above. The outer diameter of the distal side small diameter region 21 is more preferably 0.5 mm or smaller. The outer diameter of the distal side small diameter region 21 is preferably 0.35 mm or larger. Typically, the outer diameter can be 0.4 mm to 0.45 mm.

The inner diameter of the distal tip 80 (inner diameter of the distal lumen 81) and the inner diameter of the distal side small diameter region 21 (inner diameter of the lumen 31 in the distal side small diameter region 21) are preferably 0.25 mm to 0.45 mm.

The outer diameter of each wire (first wire 51 to eighth wire 58) forming the first braid 50 is preferably 5 μm to 30 μm. Typically, the outer diameter can be approximately 15 μm.

The pitch of each wire forming the first braid 50 is preferably 0.3 mm to 0.8 mm, and can be 0.5 mm or larger.

The pitch of each wire forming the first braid 50 is preferably less than twice the outer diameter of the distal portion (for example, the distal side small diameter region 21) of the catheter body 10. In this manner, bendability of the distal portion of the catheter body 10 can be satisfactorily achieved.

In a rectangular cross-sectional dimension of each wire (first wire 61 to eighth wire 68) forming the second braid 60, a short side is preferably 5 μm to 30 μm, and a long side is preferably 30 μm to 70 μm.

The pitch of each wire forming the second braid 60 is preferably 2 mm to 10 mm.

Next, examples of the material of each portion of the catheter 100 will be described.

As the material of the inner layer 32 and the inner layer 83, a resin material such as PTFE can be used.

As the material of the outer layer 33 and the outer layer 84, a nylon-based elastomer, a urethane-based elastomer, a polyester-based elastomer, or a fluorine-based resin (for example, e-PTFE) can be used. A radiopaque additive such as BaSO4 may be added to the resin material forming the outer layer 33 and the outer layer 84. The content of the additive is appropriately determined in accordance with desired physical properties such as hardness. For example, the content can be set to 20% by mass to 50% by mass, based on the total mass of the resin material forming the outer layer 33 and the outer layer 84.

The material of the marker 70 is not particularly limited as long as the material is a radiopaque metal material (for example, a platinum alloy).

As the material of each wire (first wire 51 to eighth wire 58) forming the first braid 50, for example, tungsten can be used.

As the material of each wire (first wire 61 to eighth wire 68) forming the second braid 60, for example, stainless steel (SUS304) can be used.

Next, a gripping portion 90 disposed on the proximal side of the catheter body 10 will be described. As shown in FIG. 1, the gripping portion 90 is disposed in the proximal portion of the catheter body 10. The gripping portion 90 has a connecting portion 91 for inserting an injector (syringe, not shown) from a proximal end thereof. A screw groove is formed on the outer periphery of the connecting portion 91 so that the syringe can be detachably fixed thereto. A hub 92 is disposed in a central portion of the gripping portion 90. A hollow portion is formed in the gripping portion 90 so as to penetrate the gripping portion 90 in the axial direction from the distal end to the proximal end, and the proximal portion of the catheter body 10 is inserted into the distal side portion in the hollow portion. The proximal portion of the catheter body 10 is fixed to the gripping portion 90. The hub 92 has two wing portions 93 facing each other via the axis of the gripping portion 90. The wing portion 93 is rotated around the axis of the gripping portion 90. In this manner, a torque operation for axially rotating the whole catheter body 10 can be performed, and an orientation of the distal end of the catheter body 10 entering the body cavity can be adjusted.

A protector 94 is disposed on the distal side of the hub 92 and covers the periphery of the proximal portion of the catheter body 10.

For example, the catheter 100 is a flow direct catheter that moves forward by riding on a blood flow.

The catheter 100 is typically used to perform a medical procedure as follows. The catheter 100 is inserted into the body from a femoral base artery of a subject. The distal portion of the catheter body 10 is inserted into the perforator bifurcated from the internal carotid artery via the heart and the internal carotid artery. Therefore, the catheter body 10 is manufactured to have a length corresponding to this medical procedure. However, the present invention is not limited to this example, and the catheter 100 may be manufactured to have a length suitable for inserting the catheter 100 into other sites.

Second Embodiment

Figure 9:
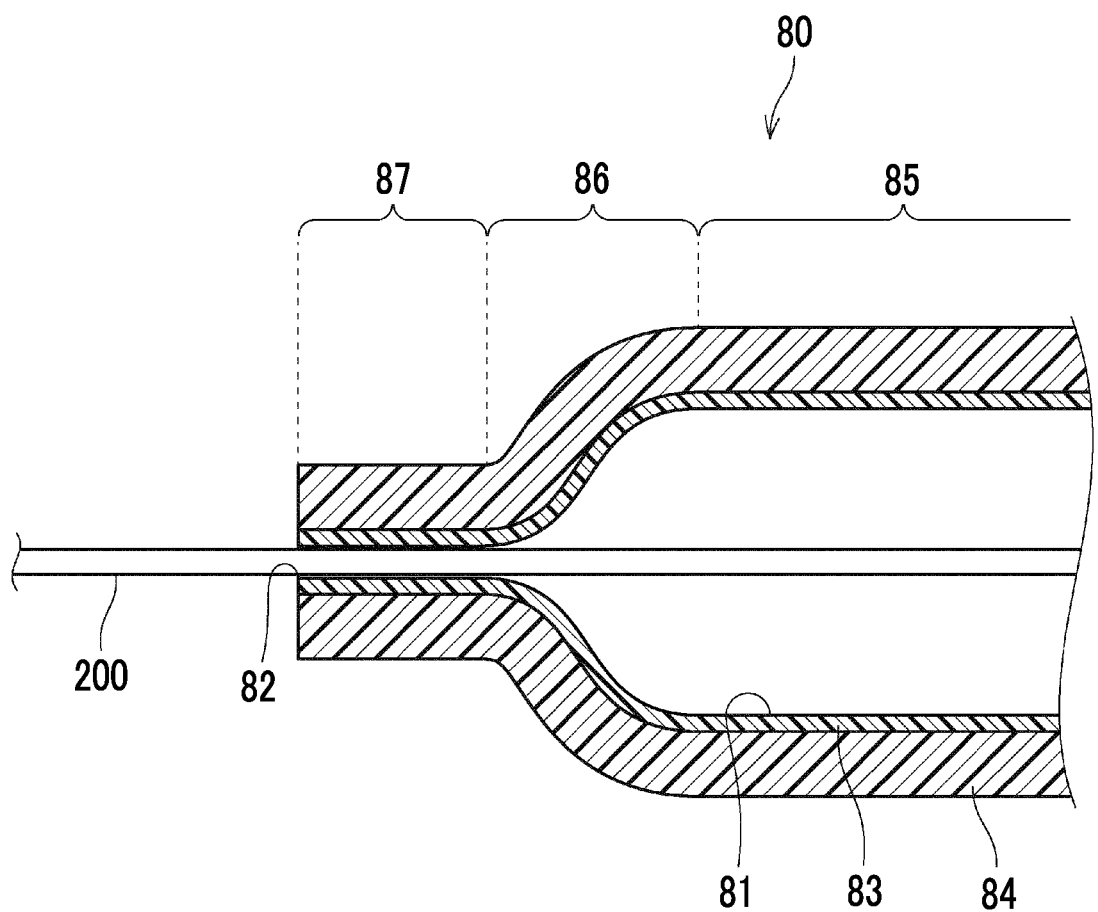
FIG. 9 is a longitudinal sectional view of a distal tip of a catheter according to a second embodiment.

Next, a second embodiment will be described with reference to FIG. 9.

The catheter according to the present embodiment (all are not shown) is different from the catheter 100 according to the first embodiment in a structure of the distal tip 80, and the other configurations are the same as those of the catheter 100 according to the first embodiment.

In a case of the present embodiment, the distal tip 80 has a first constant diameter region 85 whose outer diameter and inner diameter are constant regardless of a position of the distal tip 80 in the axial direction, a reduced diameter region 86 connected to the distal side of the first constant diameter region 85 and whose outer diameter and the inner diameter are reduced toward the distal side, and a second constant diameter region 87 connected to the distal side of the reduced diameter region 86 and whose outer diameter and inner diameter are constant regardless of the position of the distal tip 80 in the axial direction.

The outer diameter and the inner diameter of the first constant diameter region 85 are the same as the outer diameter and the inner diameter of the distal tip 80 according to the first embodiment.

A fact that the outer diameter and the inner diameter of the first constant diameter region 85 are constant regardless of the position of the distal tip 80 in the axial direction means that a change in the outer diameter and a change in the inner diameter of the first constant diameter region 85 which correspond to the position of the distal tip 80 in the axial direction respectively fall within a range of ±10%, and each of the changes preferably falls within a range of ±5%.

The outer diameter and the inner diameter of the proximal end of the reduced diameter region 86 are equal to the outer diameter and the inner diameter of the distal end of the first constant diameter region 85.

The outer diameter and the inner diameter of the reduced diameter region 86 are gradually reduced toward the distal side.

The outer diameter and the inner diameter of the proximal end of the second constant diameter region 87 are equal to the outer diameter and the inner diameter of the distal end of the reduced diameter region 86.

A fact that the outer diameter and the inner diameter of the second constant diameter region 87 are constant regardless of the position of the distal tip 80 in the axial direction means that a change in the outer diameter and a change in the inner diameter of the second constant diameter region 87 which correspond to the position of the distal tip 80 in the axial direction respectively fall within a range of ±10%, and each of the changes preferably falls within a range of ±5%.

A corner portion on the outer peripheral side of the distal end of the second constant diameter region 87 may have an R-chamfered shape. In this case, except for a distal region where the corner portion has the R-chamfered shape in the axial direction of the second constant diameter region 87, the outer diameter of the second constant diameter region 87 is constant regardless of the position of the distal tip 80 in the axial direction.

According to the present embodiment, the inner diameter of the second constant diameter region 87 of the distal tip 80 is smaller than the inner diameter of the first constant diameter region 85. Accordingly, when a medical procedure is performed using the guide wire 200, it is possible to reduce a clearance between the inner peripheral surface of the second constant diameter region 87 and the outer peripheral surface of the guide wire 200.

In this manner, a variation (fluctuation) in the relative position between the guide wire 200 and the distal tip 80 can be suppressed, and a highly accurate medical procedure can be stably performed.

When a liquid such as a drug solution is discharged from the distal opening 82 of the distal tip 80 through the lumen 31 and the distal lumen 81 of the catheter, the inner diameter of the second constant diameter region 87 is temporarily enlarged due to the pressure of the liquid, and the liquid can be smoothly discharged.

The outer diameter of the second constant diameter region 87 is preferably smaller than the inner diameter of the first constant diameter region 85.

However, the outer diameter of the second constant diameter region 87 may be equal to the inner diameter of the first constant diameter region 85, or may be larger than the inner diameter of the first constant diameter region 85.

In a case of the present embodiment, the inner diameter of the second constant diameter region 87 is equal to the outer diameter of the distal portion of the guide wire 200.

Here, a set (kit) of the catheter and the guide wire 200 according to the present embodiment is a catheter kit according to the present embodiment.

That is, the catheter kit according to the present embodiment includes an inactive type microcatheter and the guide wire 200. The catheter includes the elongated catheter body 10 (refer to FIGS. 1 to 3) having the resin layer 30 including the inner layer 32 having the lumen 31 and the outer layer 33 formed in the outer periphery of the inner layer 32, and the reinforcement layer 40 incorporated in the resin layer 30 and disposed around the lumen 31, the ring-shaped marker 70 (refer to FIGS. 1 to 3) made of a radiopaque metal material, the marker 70 being incorporated in the resin layer 30 in the distal end of the catheter body 10, fixed to the distal end of the reinforcement layer 40, and disposed around the lumen 31, and the resin-made distal tip (refer to FIG. 9) linked to the distal end of the catheter body 10, the distal tip 80 having the distal lumen 81 communicating with the lumen 31 and having the open distal end, in which the outer diameter of the distal end of the catheter body 10 is 0.6 mm or smaller and the maximum outer diameter of the distal tip is 0.6 mm or smaller. The dimension of the marker 70 in the axial direction of the catheter body 10 is smaller than the outer diameter of the distal tip 80. The length of the distal tip 80 in the axial direction of the distal tip 80 is 7 to 15 times the maximum outer diameter of the distal tip 80. In the catheter, the distal tip 80 has the first constant diameter region 85 whose outer diameter and inner diameter are constant regardless of the position of the distal tip 80 in the axial direction, the reduced diameter region 86 connected to the distal side of the first constant diameter region 85 and whose outer diameter and inner diameter are reduced toward the distal side, and the second constant diameter region 87 connected to the distal side of the reduced diameter region 86 and whose outer diameter and the inner diameter are constant regardless of the position of the distal tip 80 in the axial direction. The guide wire 200 is used with a diameter region 87, and a catheter having a guide wire 200 used by being inserted into the lumen 31. The inner diameter of the second constant diameter region 87 is equal to the outer diameter of the distal portion of the guide wire 200.

According to this catheter kit, the inner diameter of the second constant diameter region 87 is equal to the outer diameter of the distal portion of the guide wire 200. Accordingly, when a medical procedure is performed using the guide wire 200, it is possible to extremely reduce a clearance between the inner peripheral surface of the second constant diameter region 87 and the outer peripheral surface of the guide wire 200.

In this manner, a variation (fluctuation) in the relative position between the guide wire 200 and the distal tip 80 can be further suppressed, and a highly accurate medical procedure can be more stably performed.

In addition, without being limited to a case where the catheter according to the present embodiment is used in combination with the guide wire 200 of the above-described catheter kit, the catheter according to the present embodiment may be used in combination with a single product of the guide wire 200 which is not included in the kit (guide wire 200 distributed separately from the catheter according to the present embodiment).

Hitherto, each embodiment has been described with reference to the drawings. However, the embodiments are merely examples of the present invention, and various configurations other than those described above can be adopted.

For example, in each of the above-described embodiments, an example has been described in which the distal portion of the reinforcement layer is the braid (first braid 50). However, the distal portion of the reinforcement layer may be a coil configured so that a wire rod (wire) is spirally wound. In this case, the length of the distal tip 80 in the axial direction of the distal tip 80 is preferably 3 to 12 times the maximum outer diameter of the distal tip 80, and is more preferably 6 to 10 times.

In a case where the distal portion of the reinforcement layer is the coil, the braid may be disposed on the same layer as the coil on the proximal side of the coil, and the distal end of the braid and the proximal end of the coil are connected to each other by means of welding.

Alternatively, an inner reinforcement layer (reinforcement layer disposed in place of the first braid 50 in the above-described respective embodiments) may be formed of the coil over the entire length, and an outer reinforcement layer may be formed of the braid (second braid 60 in the above-described respective embodiments).

In addition, the above-described respective embodiments can be appropriately combined with each other within the scope not departing from the gist of the present invention.

Next, an example will be described to describe the present invention in more detail. However, the present invention is not limited by the following examples.

EXAMPLE 1

An intravascular surgery simulator (blood vessel model) including a simulated internal carotid artery 301 (FIG. 4A) and a simulated perforator 302 (FIG. 4A) is used so as to perform a medical procedure of causing the catheter 100 according to the first embodiment to enter the perforator 302.

The inner diameter of the internal carotid artery 301 is approximately 5 mm. The perforator 302 is bifurcated from the internal carotid artery 301. The inner diameter of the perforator 302 is approximately 0.4 mm to 0.6 mm.

Figure 4A:
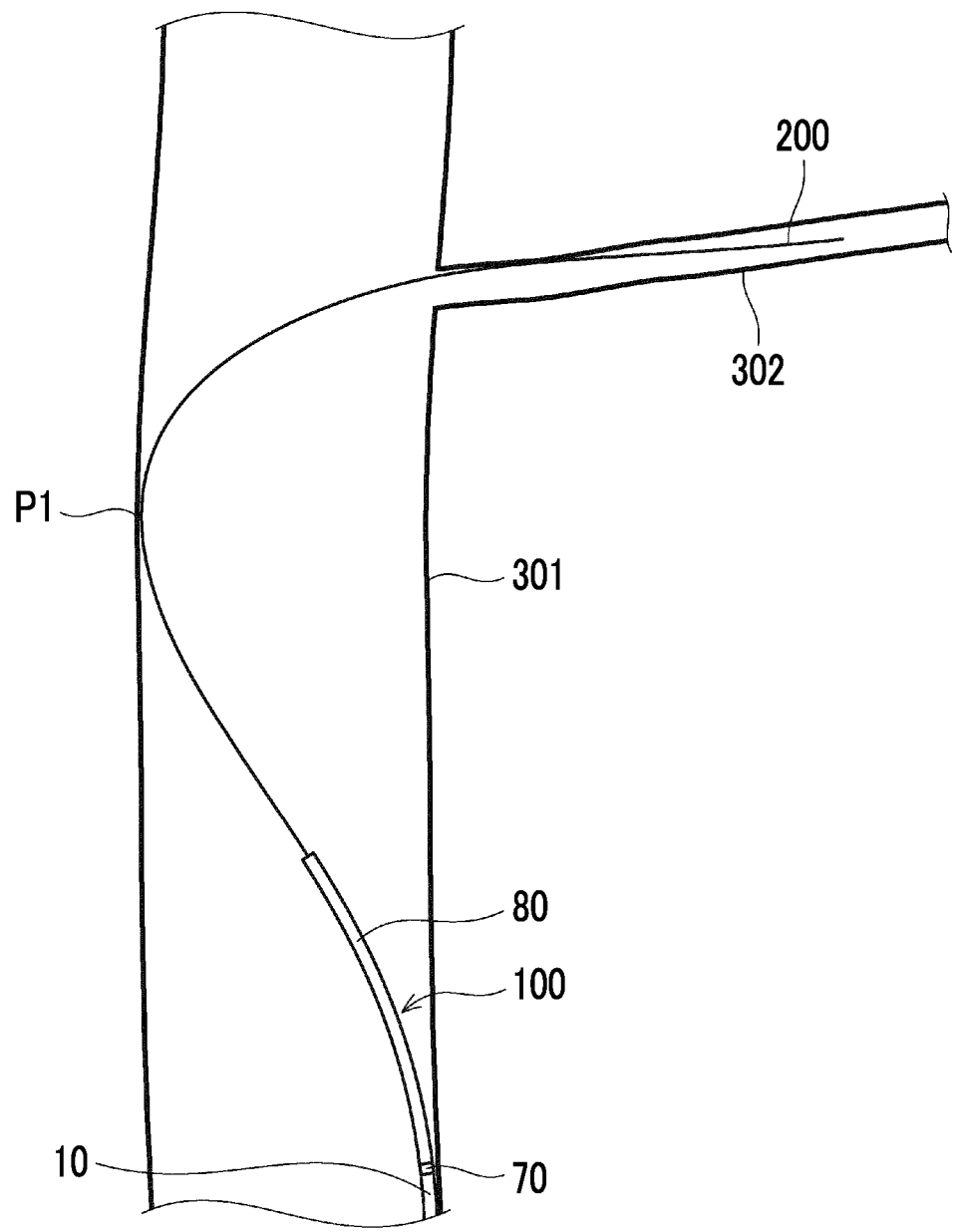
FIG. 4A is a schematic view showing a series of operations of a catheter 100 according to Example 1.

First, as shown in FIG. 4A, the catheter 100 is moved ahead, and the guide wire 200 is caused to enter the perforator 302 from the internal carotid artery 301. The distal end of the guide wire 200 is caused to reach a sufficiently deep position in the perforator 302. The distal end of the distal tip 80 is not yet caused to enter the perforator 302, and is located inside the internal carotid artery 301.

Here, the guide wire 200 comes into contact with an inner peripheral wall of the internal carotid artery 301 at a contact point P1, obtains a reaction force from the contact point P1, and enters the perforator 302 bifurcated to a side facing the contact point P1. On the other hand, the distal end of the catheter 100, that is, the distal end of the distal tip 80 does not yet reach the contact point P1 in a stage shown in FIG. 4A.

Figure 4B:
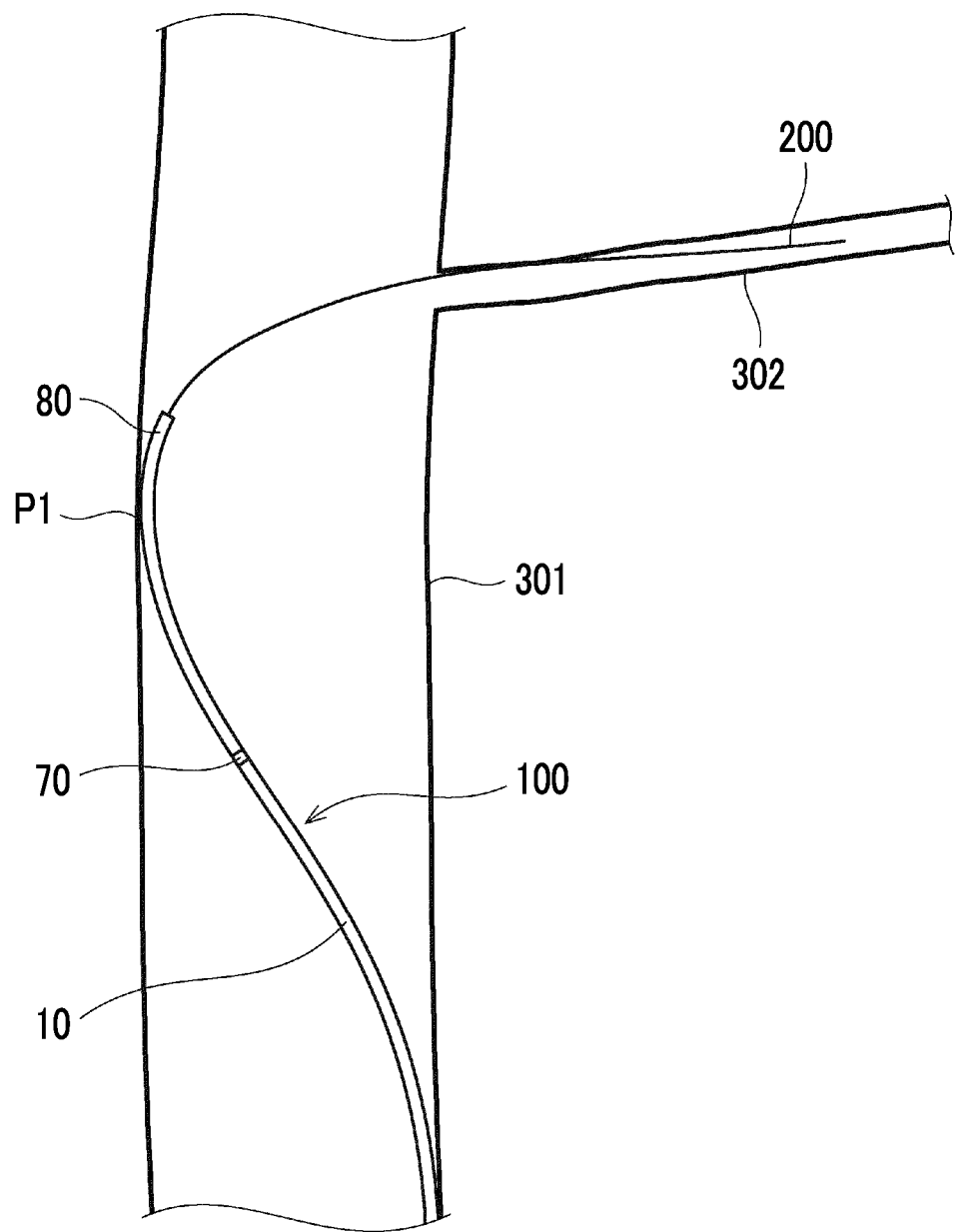
FIG. 4B is a schematic view showing a series of operations of the catheter 100 according to Example 1.

Next, as shown in FIG. 4B, the catheter 100 is pushed along the guide wire 200, and is moved forward. In a stage shown in FIG. 4B, the distal end of the distal tip 80 exceeds the contact point P1, and is located in the vicinity of the contact point P1. In addition, the marker 70 does not yet reach the contact point P1.

A portion of the guide wire 200 which is located between the contact point P1 and the perforator 302 is bent by a slight force. However, according to the present embodiment, the distal tip 80 is configured to be sufficiently soft (Shore D hardness is 40 or lower). Therefore, bending of the guide wire 200 can be suppressed when the distal tip 80 moves forward along the guide wire 200.

Figure 5A:
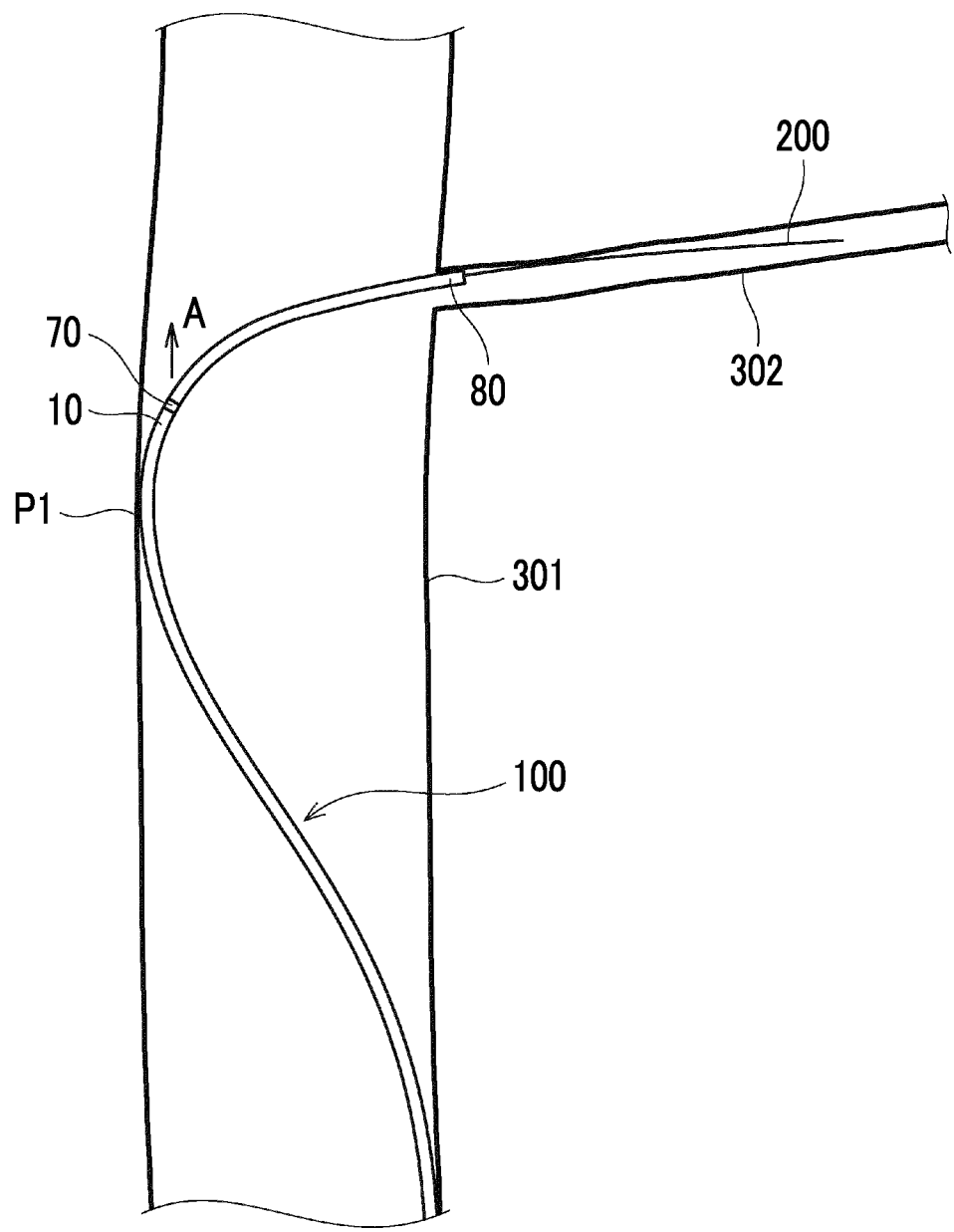
FIG. 5A is a schematic view showing a series of operations of the catheter 100 according to Example 1.
Figure 5B:
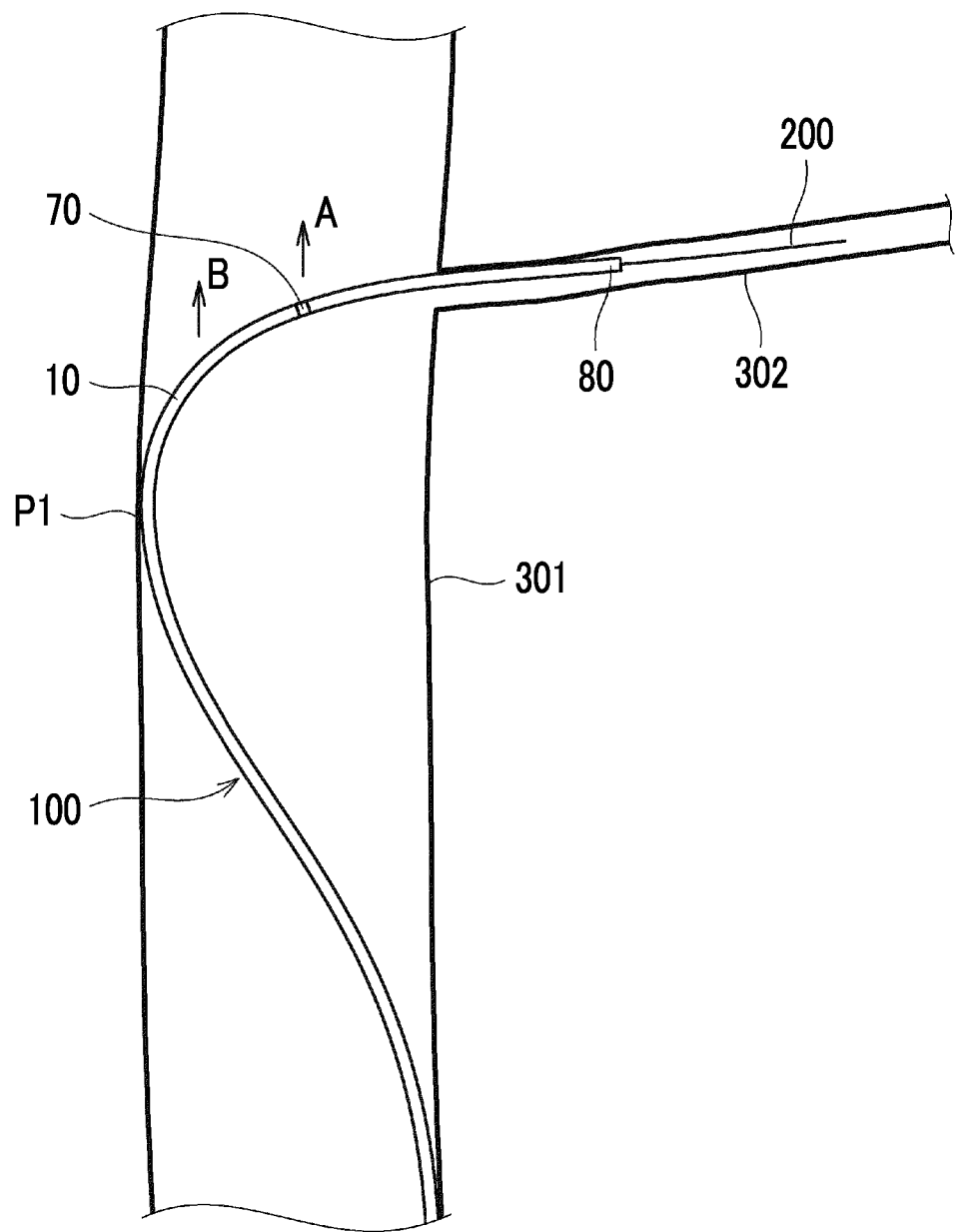
FIG. 5B is a schematic view showing a series of operations of the catheter 100 according to Example 1.

Next, as shown in FIGS. 5A and 5B, the catheter 100 is further pushed along the guide wire 200, and is further moved forward. In a stage shown in FIGS. 5A and 5B, the distal end of the distal tip 80 enters the perforator 302. In addition, the marker 70 exceeds the contact point P1.

According to the present embodiment, the length of the distal tip 80 in the axial direction is 5 mm, the maximum outer diameter of the distal tip 80 is 0.45 mm, and the length of the marker 70 in the axial direction of the catheter body 10 is 0.3 mm. The sufficiently soft distal tip 80 has a sufficient length (7 times or more the maximum outer diameter of the distal tip 80), and the marker 70 is sufficiently short (dimension of the marker 70 in the axial direction of the catheter body 10 is smaller than the maximum outer diameter of the distal tip 80). Accordingly, in a process of causing the distal end of the distal tip 80 to enter the perforator 302, the bending caused by a fact that the portion of the guide wire 200 which is located between the contact point P1 and the perforator 302 is pressed by the catheter 100 is suppressed. That is, when the marker 70 exceeds the contact point P1 or after the marker 70 exceeds the contact point P1 as shown in FIGS. 5A and 5B, it is possible to suppress a force of the marker 70 to press the portion located between the contact point P1 and the perforator 302 in the guide wire 200 upward (in a direction of an arrow A) in FIGS. 5A and 5B. Therefore, while the distal tip 80 is caused to satisfactorily follow a bent shape of the guide wire 200, the distal tip 80 can enter the perforator 302 along the guide wire 200.

In addition, the reinforcement layer 40 disposed in the distal portion of the catheter body 10 is configured to include the braid (first braid 50) in which the wires are braided, and the pitch of the wires is 0.8 mm. The outer diameter of the distal portion of the catheter body 10 is 0.5 mm. That is, in the portion of the catheter body 10 which is connected to the proximal side of the marker 70, the pitch of the wires forming the first braid 50 is set to be less than twice the outer diameter of the distal portion of the catheter body 10.

In this manner, as shown in FIGS. 5A and 5B, when the catheter 100 moves forward while the portion connected to the proximal side of the marker 70 in the catheter body 10 comes into contact with the contact point P1, the portion of the catheter body 10 which comes into contact with the contact point P1 can be smoothly bent.

That is, the catheter body 10 has the first braid 50. Accordingly, although bending rigidity of the catheter body 10 is higher than bending rigidity of the distal tip 80, the pitch of the wires of the first braid 50 is sufficiently small. Therefore, the first braid 50 and the catheter body 10 can be smoothly bent by a reaction force received from the contact point P1. In particular, the cross-sectional shape of the wire forming the first braid 50 is circular. Accordingly, the wires can be easily and slightly rotated (rolled) at an intersection point of the wires. Therefore, the first braid 50 and the catheter body 10 can be more smoothly bent.

Therefore, it is possible to suppress the force of the catheter body 10 to press the portion of the guide wire 200 which is located between the contact point P1 and the perforator 302 upward (in a direction of an arrow B shown in FIG. 5B) in FIGS. 5A and 5B.

Figure 6:
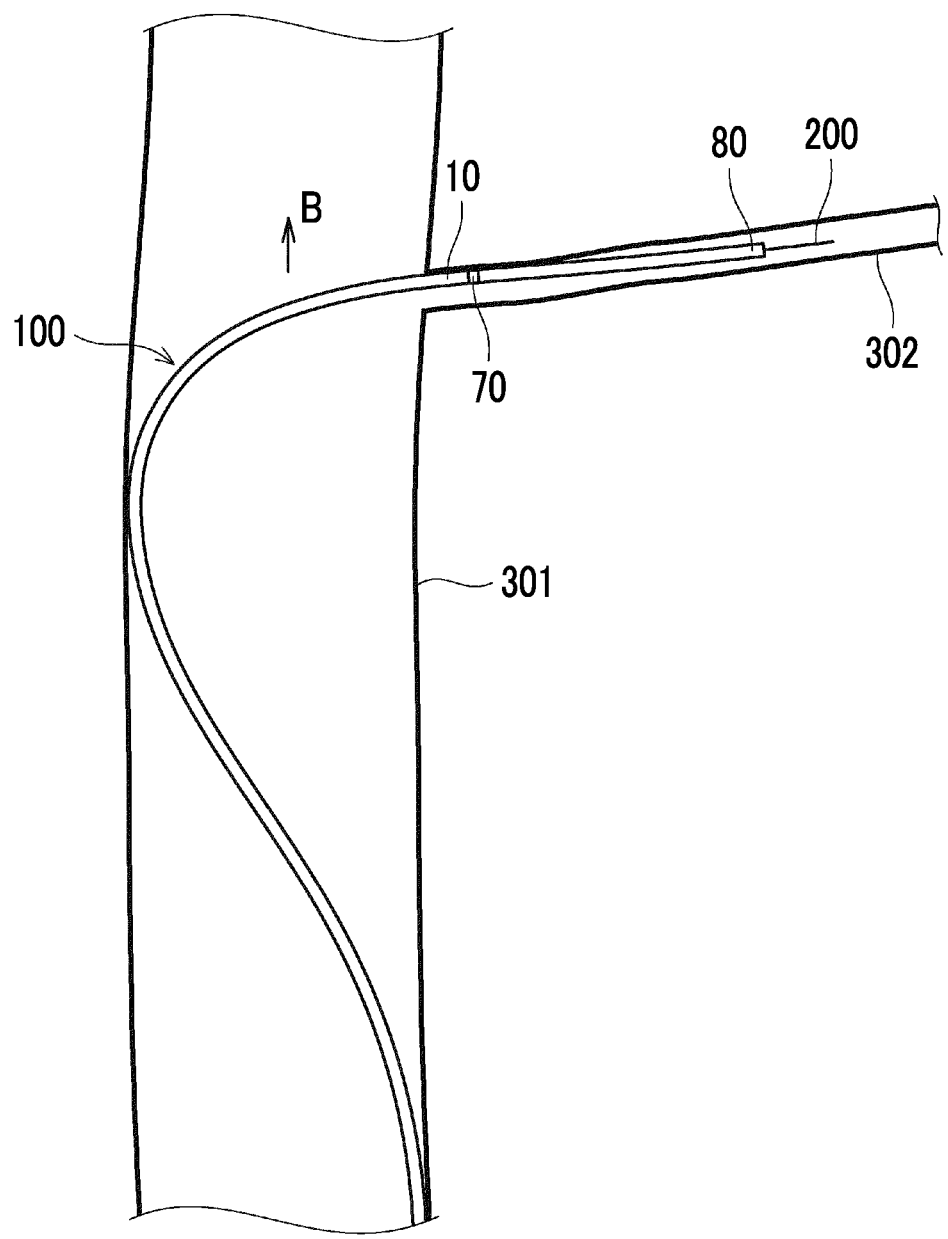
FIG. 6 is a schematic view showing a series of operations of the catheter 100 according to Example 1.

As a result, as shown in FIG. 6, the distal end of the catheter body 10, that is, a disposition region of the marker 70 can smoothly enter the perforator 302.

EXAMPLE 2

As in Example 1, the intravascular surgery simulator (blood vessel model) including the simulated internal carotid artery 301 (FIG. 7A) and the simulated perforator 302 (FIG. 7A) is used to perform the medical procedure of causing the catheter 100 according to the first embodiment to enter the perforator 302.

Figure 7A:
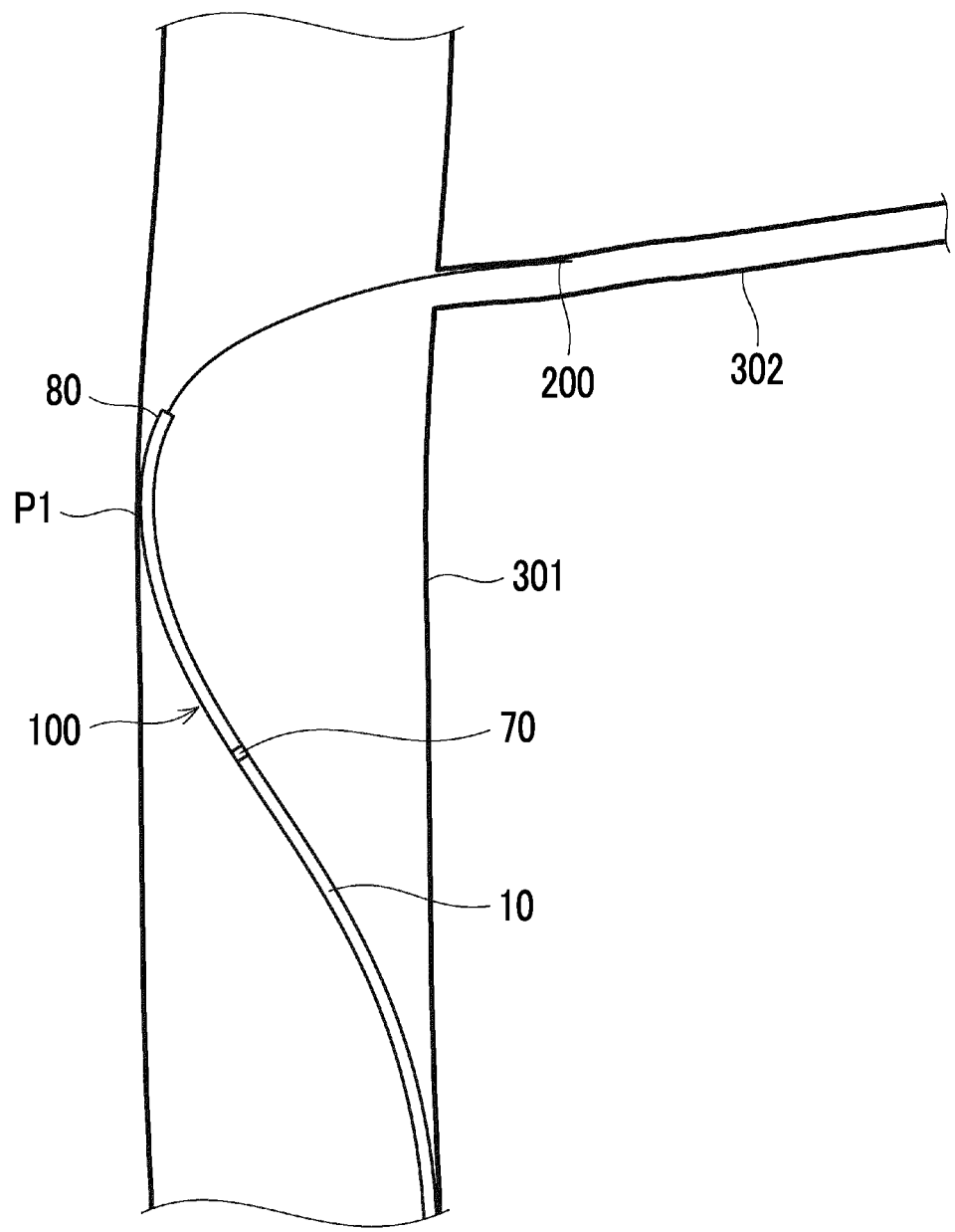
FIG. 7A is a schematic view showing a series of operations of the catheter 100 according to Example 2.

First, as shown in FIG. 7A, the catheter 100 is moved ahead, and the guide wire 200 is caused to enter the perforator 302 from the internal carotid artery 301. The distal end of the guide wire 200 is caused to reach the vicinity of the entrance of the perforator 302. The distal end of the distal tip 80 is not yet caused to enter the perforator 302, and is located inside the internal carotid artery 301.

Figure 7B:
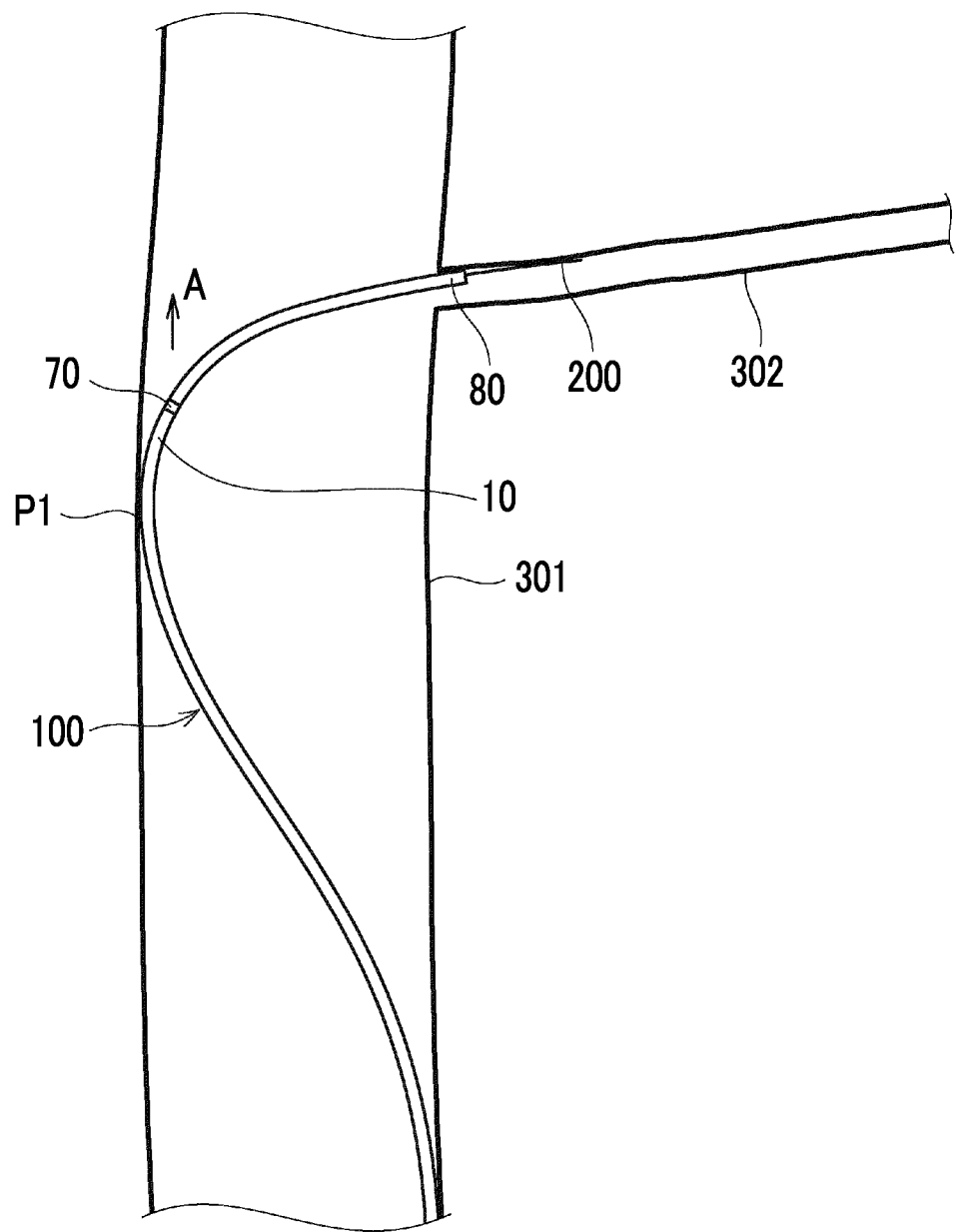
FIG. 7B is a schematic view showing a series of operations of the catheter 100 according to Example 2.

Next, as shown in FIG. 7B, the catheter 100 is pushed along the guide wire 200, and is moved forward. In a stage shown in FIG. 7B, the distal end of the distal tip 80 enters the perforator 302, and the marker 70 exceeds the contact point P1.

Figure 8:
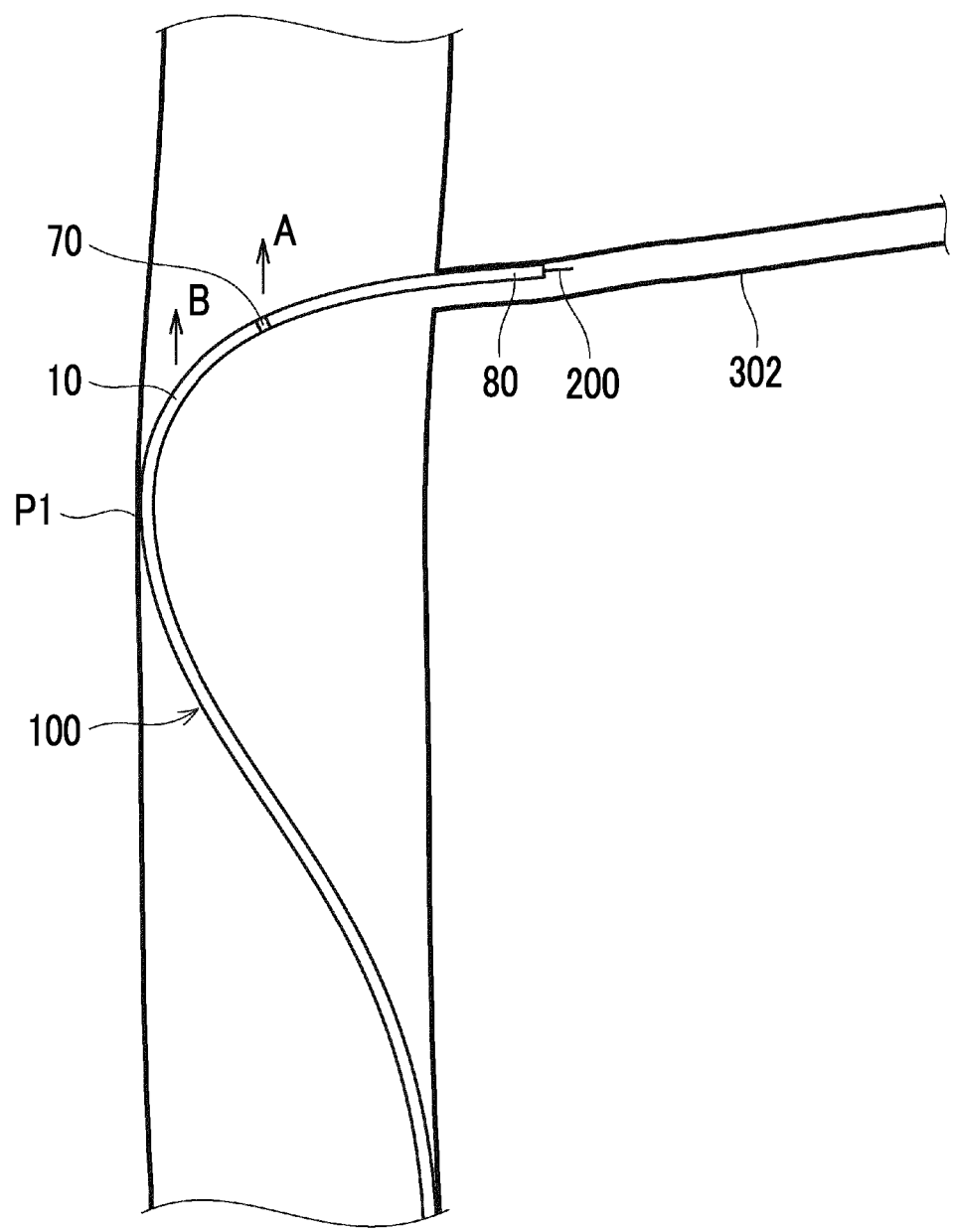
FIG. 8 is a schematic view showing a series of operations of the catheter 100 according to Example 2.

As in Example 1, when the marker 70 exceeds the contact point P1 or after the marker 70 exceeds the contact point P1, the force of the marker 70 to press the portion located between the contact point P1 and the perforator 302 in the guide wire 200 upward (direction of the arrow A) in FIGS. 7A and 7B or the force of the catheter body 10 to press the portion upward (direction of the arrow B) in FIGS. 7A and 7B is suppressed. Accordingly, as shown in FIG. 8, the distal end of the catheter body 10 can smoothly enter the perforator 302.

COMPARATIVE EXAMPLE 1

As a microcatheter (hereinafter, a catheter 400: FIGS. 10A, 10B, 11A, 11B, and 12), a commercially available microcatheter having relatively good vascular selectivity is representatively used. As in Example 1, the intravascular surgery simulator including the simulated internal carotid artery 301 and the simulated perforator 302 is used to perform the medical procedure of causing the catheter 400 to enter the perforator 302.

In the catheter 400, the length of the distal tip 480 in the axial direction is smaller than one time the maximum outer diameter of the distal tip 480, and the length of the marker 470 in the axial direction of the catheter body 410 is larger than the maximum outer diameter of the distal tip 480. Compared to the catheter 100 according to the present embodiment, a length ratio of a distal tip 480 is significantly decreased, and a length ratio of a marker 470 is increased. In addition, a structure is adopted in which the reinforcement layer extends from the marker 470 toward the proximal side.

Figure 10A:
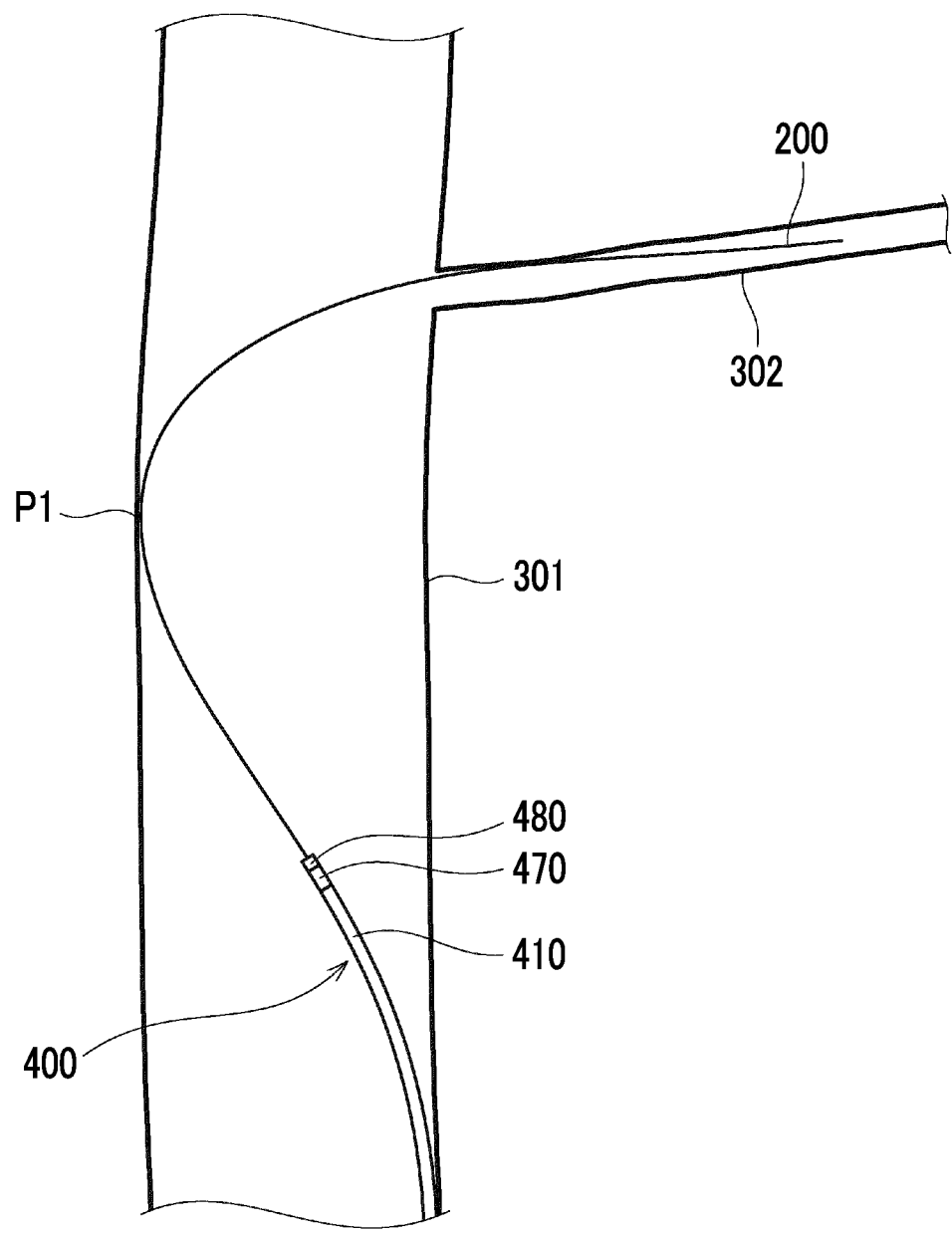
FIG. 10A is a schematic view showing a series of operations of a catheter 400 according to Comparative Example 1.

In a stage shown in FIG. 10A, as in the stage shown in FIG. 4A, the catheter 400 is moved ahead, and the guide wire 200 enters the perforator 302 from the internal carotid artery 301. The distal end of the distal tip 480 is not yet caused to enter the perforator 302, is located inside the internal carotid artery 301, and does not yet reach the contact point P1.

The catheter 400 has a structure as follows. The marker 470 is located in the vicinity of the distal end of the catheter 400, the axial length of the marker 470 is long, the reinforcement layer extends from the marker 470 toward the proximal side, and the rigidity is improved up to the vicinity of the distal end of the catheter 400.

Therefore, when the catheter 400 is pushed along the guide wire 200 from the stage shown in FIG. 10A, a portion of the guide wire 200 which is located between the contact point P1 and the perforator 302 is pressed against the distal portion of the catheter 400, and is bent. In some cases, the guide wire 200 is separated from the perforator 302.

In addition, in some cases, the distal portion of the catheter 400 is caught on the inner peripheral surface of the internal carotid artery 301 at the contact point P1, and is not moved forward any further.

Figure 10B:
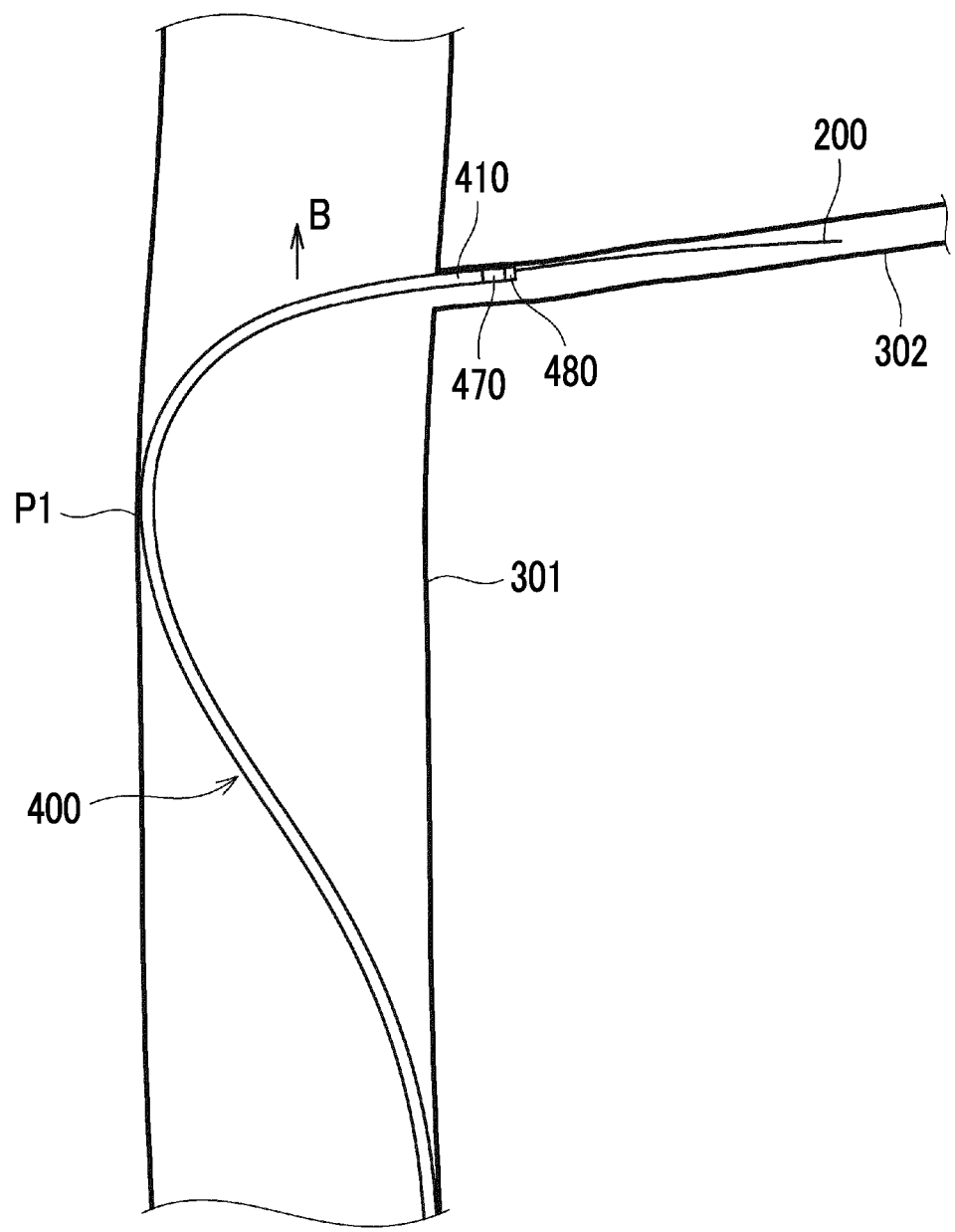
FIG. 10B is a schematic view showing a series of operations of the catheter 400 according to Comparative Example 1.

In addition, as shown in FIG. 10B, in a case where the catheter 400 is pushed along the guide wire 200 and the distal end of the distal tip 480 can enter the vicinity of the entrance of the perforator 302, as described below, the catheter 400 cannot more deeply enter the perforator 302, or the guide wire 200 and the catheter 400 are eventually separated from the perforator 302, in some cases.

Figure 11A:
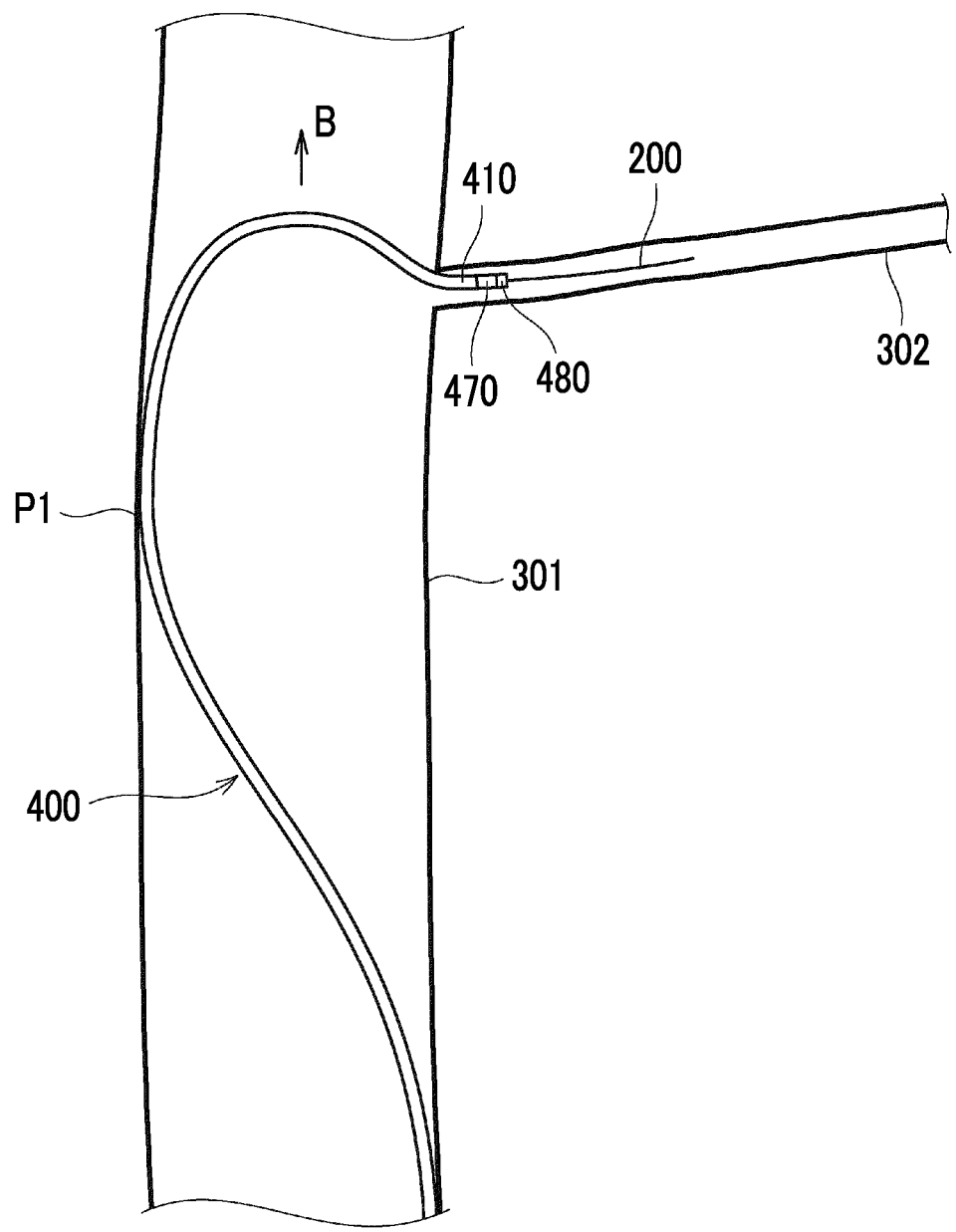
FIG. 11A is a schematic view showing a series of operations of the catheter 400 according to Comparative Example 1.
Figure 11B:
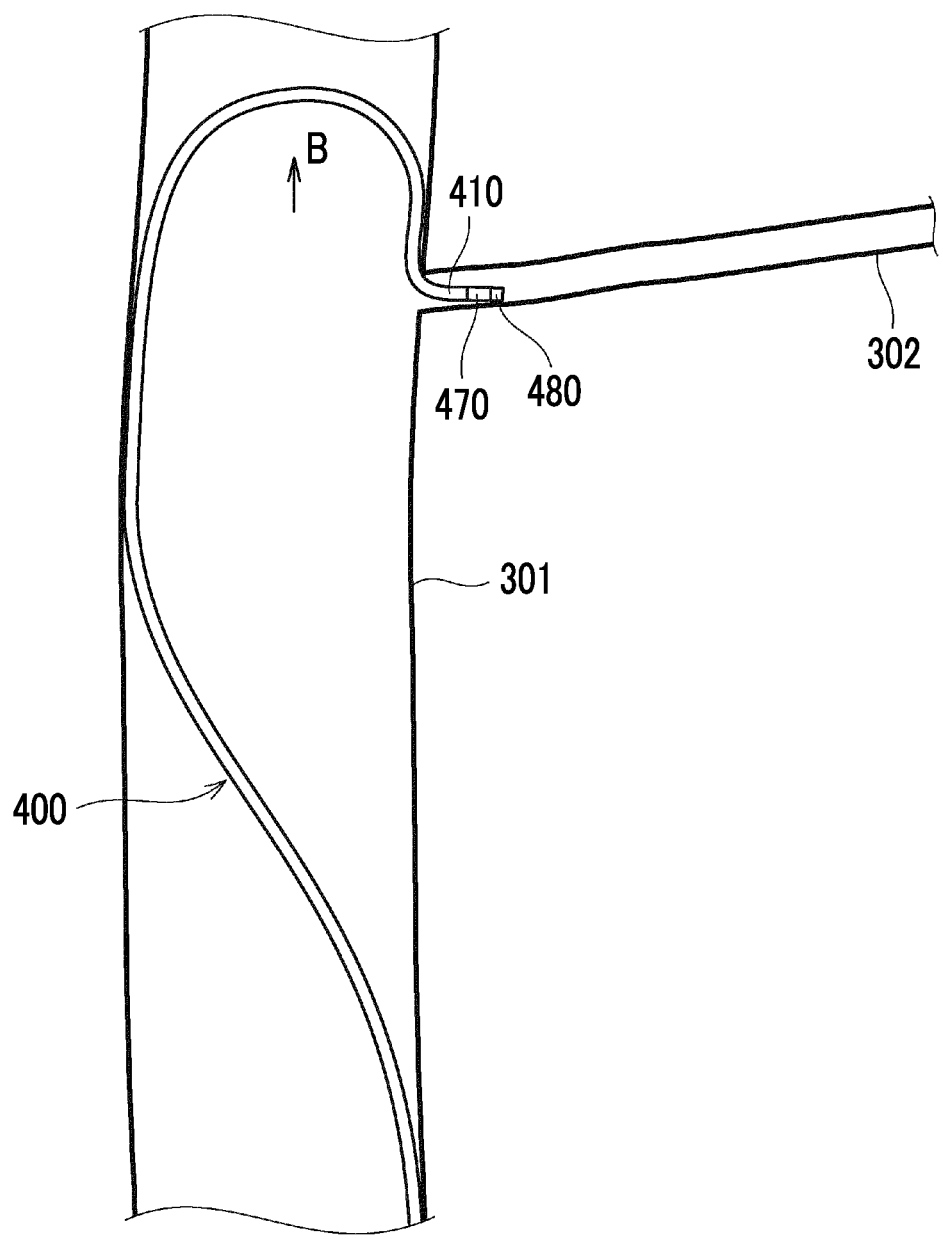
FIG. 11B is a schematic view showing a series of operations of the catheter 400 according to Comparative Example 1.

That is, as shown in FIG. 10B, after the distal end of the distal tip 480 enters the vicinity of the entrance of the perforator 302, even if the catheter 400 is further pushed as shown in FIGS. 11A and 11B, the distal portion of the catheter 400 is caught on the vicinity of the entrance of the perforator 302, and the catheter body 410 is bent in the direction of the arrow B in FIGS. 11A and 11B. In this case, the distal portion of the guide wire 200 is gradually drawn into the catheter 400.

The reason for the operation is considered as follows. The distal tip 480 which is a soft portion of the distal portion of the catheter 400 is short. Accordingly, the distal portion of the catheter 400 is stiffened, protruded, and caught on the wall surface of the entrance of the perforator 302.

Furthermore, the flexibility of the distal portion of the catheter 400 is poor. Accordingly, in a state where the distal portion of the catheter 400 is bent, the force of pushing the catheter 400 is applied in a forward moving direction of the catheter 400 on the proximal side of the bent portion. Accordingly, there is a high ratio that the pushing force is consumed in the lateral movement (direction intersecting the longitudinal direction) instead of the vertical movement (longitudinal direction) of the distal portion. This fact is also considered as the reason of the operation shown in FIGS. 11A and 11B.

Figure 12:
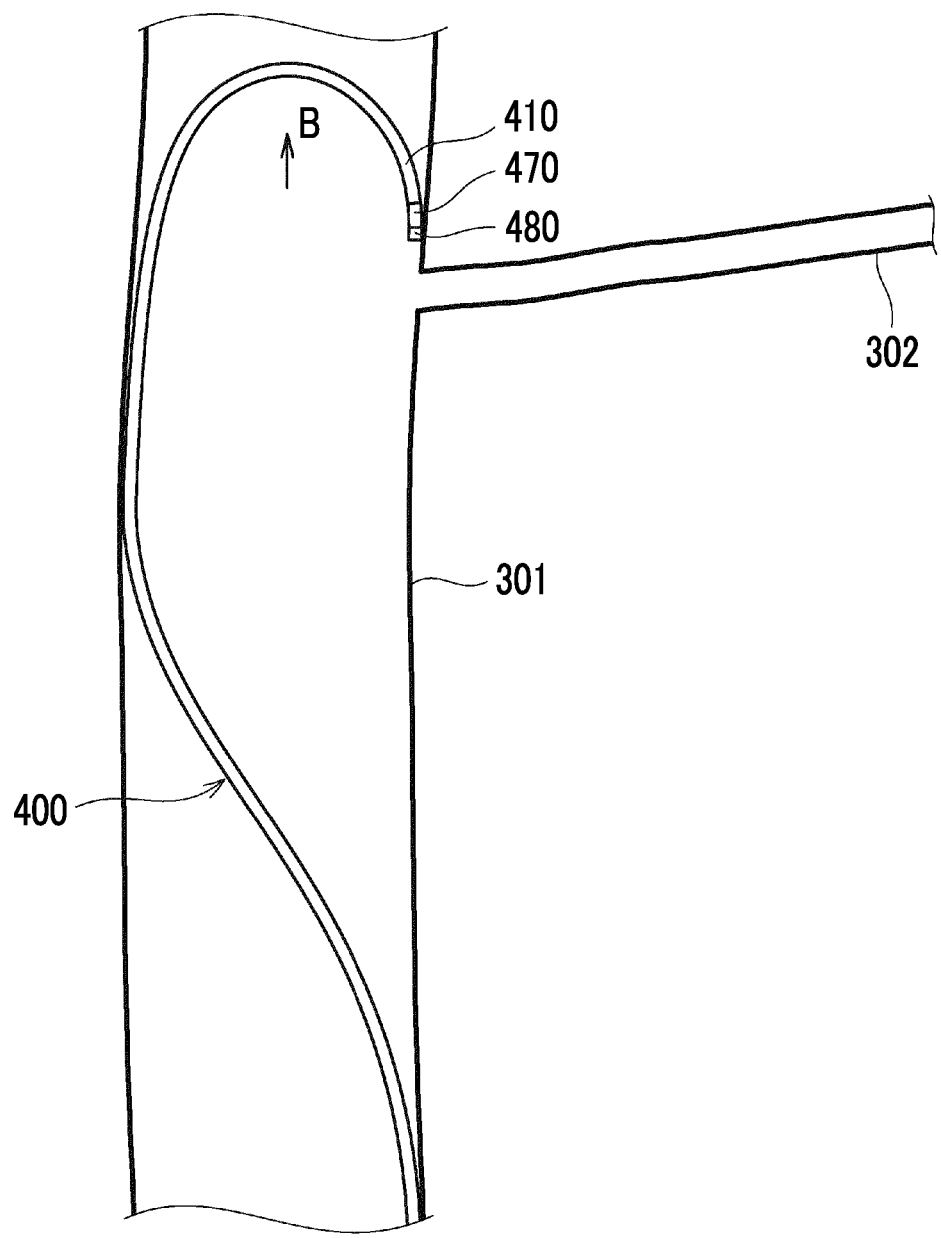
FIG. 12 is a schematic view showing a series of operations of the catheter 400 according to Comparative Example 1.

When the catheter 400 is further pushed thereafter, as shown in FIG. 12, the catheter 400 once entering the vicinity of the entrance of the perforator 302 falls off from the perforator 302, and is further pushed in the direction of the arrow B inside the internal carotid artery 301.

INDUSTRIAL APPLICABILITY

According to the present invention, a medical procedure can be preferably performed so that the catheter is guided by the guide wire to enter the narrow blood vessel such as the perforator, the AVM, the vertebral artery, or the vasa vasorum connected to the tumor.

REFERENCE SIGNS LIST

10: catheter body
11: first distal region
12: second distal region
13: third distal region
14: fourth distal region
15: fifth distal region
16: sixth distal region
17: intermediate/proximal region
21: distal side small diameter region
22: enlarged diameter region
23: small diameter region
24: large diameter region
25: outer diameter change region
30: resin layer
31: lumen
32: inner layer
33: outer layer
40: reinforcement layer
50: first braid (braid)
51: first wire
52: second wire
53: third wire
54: fourth wire
55: fifth wire
56: sixth wire
57: seventh wire
58: eighth Wire
60: second braid
61: first wire
62: second wire
63: third wire
64: fourth wire
65: fifth wire
66: sixth wire
67: seventh wire
68: eighth wire
70: marker
80: distal tip
81: distal lumen
82: distal opening
83: inner layer
84: outer layer
85: first constant diameter region
86: reduced diameter region
87: second constant diameter region
90: gripping portion
91: connecting portion
92: hub
93: wing portion
94: protector
100: catheter
200: guide wire
301: internal carotid artery
302: perforator
400: catheter
410: catheter body
470: marker
480: distal tip

What is claimed is:
1. A catheter, comprising:
   a catheter body having a lumen and comprising a resin layer and a reinforcement layer formed in the resin layer and positioned around the lumen;
   a ring-shaped marker comprising a radiopaque metal material and formed in the resin layer in a distal end of the catheter body such that the ring-shaped marker is fixed to a distal end of the reinforcement layer and positioned around the lumen; and a distal tip comprising a resin linked to the distal end of the catheter body and having a distal lumen such that the distal lumen communicates with the lumen and has an open distal end and that Shore D hardness of the distal tip is set in a range of 20 to 40, wherein the resin layer of the catheter body includes an inner layer forming the lumen and an outer layer formed in an outer periphery of the inner layer, an outer diameter of the distal end of the catheter body is 0.6 mm or smaller, and a maximum outer diameter of the distal tip is 0.6 mm or smaller, a dimension of the ring-shaped marker in an axial direction of the catheter body is smaller than a maximum outer diameter of the distal tip, a length of the distal tip in the axial direction of the distal tip is in a range of 3 times to 18 times the maximum outer diameter of the distal tip, the reinforcement layer comprises a first braid and a second braid braided in an outer periphery of the first braid such that the reinforcement layer includes the first braid and second braid in an intermediate portion and a proximal side portion of the reinforcement layer in a longitudinal direction of the catheter body and that a cross-sectional area of each wire forming the second braid is larger than a cross-sectional area of each wire forming the first braid.

2. The catheter according to claim 1, wherein the reinforcement layer has a portion in a distal portion of the catheter body such that the portion includes a braid in which wires are braided, and that a pitch of the wires is larger than an outer diameter of the distal portion of the catheter body.

3. The catheter according to claim 1, wherein an outer diameter of the distal tip is constant in an axial direction.

4. The catheter according to claim 1, wherein the distal tip has a first constant diameter region whose outer diameter and inner diameter are constant in the axial direction, a reduced diameter region connected to a distal side of the first constant diameter region and whose outer diameter and inner diameter are reduced toward the distal side, and a second constant diameter region connected to a distal side of the reduced diameter region and whose outer diameter and inner diameter are constant in the axial direction.

5. The catheter according to claim 1, wherein the catheter body has a first distal region connected to a proximal side of the distal tip, and a second distal region connected to a proximal side of the first distal region, the first distal region is made of a resin material which is the same as the resin of the distal tip, the second distal region is made of a resin material which is harder than the resin material forming the first distal region, and the reinforcement layer is continuously positioned throughout the first distal region and the second distal region.

6. The catheter according to claim 5, wherein the catheter body has an enlarged diameter region in which an inner diameter of the lumen and an outer diameter of the catheter body are gradually enlarged toward the proximal side such that the enlarged diameter region is formed on the proximal side from the second distal region.

7. The catheter according to claim 6, wherein the resin layer is made of a same resin material in a region from the distal side of the enlarged diameter region to the proximal side of the enlarged diameter region in the catheter body.

8. The catheter according to claim 6, wherein a region adjacent to the proximal side of the enlarged diameter region in the catheter body is a small diameter region having the same outer diameter as the proximal end of the enlarged diameter region, and a region adjacent to a proximal side of the small diameter region in the catheter body is a large diameter region having a larger diameter than the small diameter region.

9. A catheter kit, comprising:
the catheter of claim 4; and
a guide wire configured to be inserted into the lumen,
wherein the inner diameter of the second constant diameter region is the same as an outer diameter of a distal portion of the guide wire.

10. The catheter according to claim 7, wherein a region adjacent to the proximal side of the enlarged diameter region in the catheter body is a small diameter region having the same outer diameter as the proximal end of the enlarged diameter region, and a region adjacent to a proximal side of the small diameter region in the catheter body is a large diameter region having a larger diameter than the small diameter region.

11. The catheter according to claim 2, wherein an outer diameter of the distal tip is constant in an axial direction.

12. The catheter according to claim 2, wherein the distal tip has a first constant diameter region whose outer diameter and inner diameter are constant in the axial direction, a reduced diameter region connected to a distal side of the first constant diameter region and whose outer diameter and inner diameter are reduced toward the distal side, and a second constant diameter region connected to a distal side of the reduced diameter region and whose outer diameter and inner diameter are constant in the axial direction.

13. The catheter according to claim 2, wherein the catheter body has a first distal region connected to a proximal side of the distal tip, and a second distal region connected to a proximal side of the first distal region, the first distal region is made of a resin material which is the same as the resin of the distal tip, the second distal region is made of a resin material which is harder than the resin material forming the first distal region, and the reinforcement layer is continuously positioned throughout the first distal region and the second distal region.

14. The catheter according to claim 13, wherein the catheter body has an enlarged diameter region in which an inner diameter of the lumen and an outer diameter of the catheter body are gradually enlarged toward the proximal side such that the enlarged diameter region is formed on the proximal side from the second distal region.

15. The catheter according to claim 14, wherein the resin layer is made of a same resin material in a region from the distal side of the enlarged diameter region to the proximal side of the enlarged diameter region in the catheter body.

16. The catheter according to claim 14, wherein a region adjacent to the proximal side of the enlarged diameter region in the catheter body is a small diameter region having the same outer diameter as the proximal end of the enlarged diameter region, and a region adjacent to a proximal side of the small diameter region in the catheter body is a large diameter region having a larger diameter than the small diameter region.

17. A catheter, comprising:
a catheter body having a lumen and comprising a resin layer and a reinforcement layer formed in the resin layer and positioned around the lumen;
a ring-shaped marker comprising a radiopaque metal material and formed in the resin layer in a distal end of the catheter body such that the ring-shaped marker is fixed to a distal end of the reinforcement layer and positioned around the lumen; and a distal tip comprising a resin linked to the distal end of the catheter body and having a distal lumen such that the distal lumen communicates with the lumen and has an open distal end, wherein the resin layer of the catheter body includes an inner layer forming the lumen and an outer layer formed in an outer periphery of the inner layer, an outer diameter of the distal end of the catheter body is 0.6 mm or smaller, and a maximum outer diameter of the distal tip is 0.6 mm or smaller, a dimension of the ring-shaped marker in an axial direction of the catheter body is smaller than a maximum outer diameter of the distal tip, a length of the distal tip in the axial direction of the distal tip is in a range of 3 times to 18 times the maximum outer diameter of the distal tip, and the reinforcement layer comprises a braid comprising a plurality of wires such that the ring-shaped marker is fixed to the braid in the distal end of the reinforcement layer.

18. The catheter according to claim 17, wherein the ring-shaped marker is positioned around the inner layer of the resin layer such that the ring-shaped marker is coaxial with the inner layer and outer layer of the resin layer.

19. The catheter according to claim 17, wherein the ring-shaped marker is fixed on an outer periphery of the braid in the distal end of the reinforcement layer.

20. The catheter according to claim 17, wherein the ring-shaped marker is fixed to a distal side of the braid in the distal end of the reinforcement layer.

\* \* \* \* \*